United States Patent [19]
Tanaka et al.

[11] 4,029,508
[45] June 14, 1977

[54] SILVER HALIDE MATERIAL CONTAINING A YELLOW COLOR-FORMING COUPLER

[75] Inventors: Mitsugu Tanaka; Atsuaki Arai; Kiyoshi Nakazyo; Keisuke Shiba, all of Minami-ashigara, Japan

[73] Assignee: Fuji Photo Film Co., Ltd., Minami-ashigara, Japan

[22] Filed: Aug. 14, 1975

[21] Appl. No.: 604,861

[30] Foreign Application Priority Data

Aug. 14, 1974 Japan .............................. 49-92894

[52] U.S. Cl. ............................. 96/56.3; 96/56.4; 96/56.5; 96/74; 96/100; 260/244 R
[51] Int. Cl.² ..................... G03C 7/00; G03C 1/40
[58] Field of Search ................. 96/100, 56.2, 56.3, 96/56.4, 56.5, 74; 260/244 R

[56] References Cited
UNITED STATES PATENTS 3,619,195  11/1971  Van Campen ................. 96/100
3,620,745  11/1971  Seymour ........................ 96/100
3,767,653  10/1973  Krapcho ..................... 260/244 R Primary Examiner—J. Travis Brown
Attorney, Agent, or Firm—Sughrue, Rothwell, Mion, Zinn & Macpeak

[57] ABSTRACT

A yellow color forming photographic coupler represented by the following general formula (I):

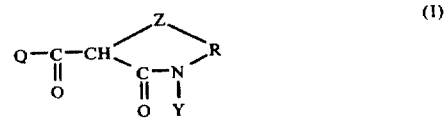

wherein Q represents an aliphatic group, an alicyclic group, an aromatic group or a heterocyclic group; Y represents a hydrogen atom, an aliphatic group, an alicyclic group, an aromatic group or a heterocyclic group; R represents a divalent aliphatic group, a divalent alicyclic group, a divalent aromatic group or a divalent heterocyclic group; and Z represents an oxygen atom, a sulfur atom or a nitrogen atom substituted with an electron attracting group.

13 Claims, No Drawings

SILVER HALIDE MATERIAL CONTAINING A YELLOW COLOR-FORMING COUPLER

BACKGROUND OF THE INVENTION

1. Field of the Invention

The present invention relates to a photographic coupler, and more particularly to a novel yellow color forming coupler which is suitable for use in the formation of color photographic images.

2. Description of the Prior Art

In the formation of color photographic images by a subtractive color reproduction process, an aromatic primary amine compound, especially an N,N-disubstituted para-phenylenediamine compound, is used as a developing agent, to reduce the exposed silver halide grains in an exposed photographic emulsion layer, and the concurrently produced oxidation product of the developing agent is coupled with the color forming coupler to form a cyan, magenta or yellow image dye.

Couplers for use in the color developing process are compounds which have a phenolic hydroxy group, an anilinic amino group or an acitve methylene group, and, by coupling with the oxidation product of the aromatic primary amine developing agent form dyes which absorb light in the visible wave length range.

The yellow dye images exhibit a specific absorption to blue light in the wave length region ranging from about 400 to 500 millimicrons. Previously known yellow color foming couplers include $\beta$-ketoacetoacetic esters, $\beta$-diketones, N,N-malonic diamides and $\alpha$-acylacetamides, and the like.

Of these compounds, benzoyl acetanilide type compounds as described in C. E. K. Mees & T. H. James, *The Theory of the Photographic Process*, 3rd. Ed., Macmillan, New York (1966) and pivaloyl acetanilide type couplers as described in U.S. Pat. No. 3,265,506 are widely used, as yellow color forming couplers, in the field of color photography. Of these couplers, a large number of the so-called two-equivalent couplers which have a coupling off group at the reactive coupling position thereof are also well known. Examples of two-equivalent couplers having various kinds of coupling off groups are disclosed in U.S. Pat. Nos. 3,447,928; 3,408,194; 3,415,652 and 3,227,155, German Patent Application (OLS) Nos. 2,213,461 and 2,219,917, U.S. Pat. No. 3,253,924, etc. Although these couplers have many preferred properties, they also have a number of disadvantages and are by no means completely satisfactory. For instance, these couplers have poor coupling reactivity, the dyes which are formed from these couplers upon color development with certain useful color developing agents have poor fastness to light, heat or humidity, these couplers have a broad absorption in a longer wave length range, resulting in poor color reproduction, and the coupling off groups leach out from a emulsion layer to a developer solution during color development and adversely affect the properties and storability of the developer solution. Furthermore, the molecular weight of the coupling off groups is large and thus the total molecular weight of the couplers is large, which is disadvantageous in decreasing the thickness of the emulsion layer which is required to improve the sharpness of the image and to shorten the processing time. For example, $\alpha$-[4-(4-benzyloxyphenylsulfonyl)-phenoxy]-$\alpha$-pivaloyl-2-chloro-5[$\gamma$-(2,4-di-tert-amylphenoxy) butyramidoacetanilide] disclosed in U.S. Pat. No. 3,408,194, $\alpha$-(3-benzyl-2,5-dioxo-1-imidazolidinyl)-$\alpha$-pivaloyl-2-chloro-5-[$\gamma$-(2,4-ditert-amylphenoxy) butyramido]-acetanilide disclosed in Japanese Patent Application (OPI) No. 29432/1973 and $\alpha$-(5,5-dimethyl-2,4-oxazolidinedione)-$\alpha$-pivaloyl-2-chloro-5[$\alpha$-(2,4-di-tert-amylphenoxy)butyramido]acetanilide disclosed in Japanese Patent Application No. 66835/1974 have good properties but their molecular weights are 908.5, 758.5 and 685.5 respectively, and the weight ratio of the coupling off group in the total molecular weight are 37.3%, 24.9% and 16.9%, respectively. As described above, the weight ratio of the coupling off group which is released upon coupling reaction to form a dye is relatively large with respect to the total molecular weight.

SUMMARY OF THE INVENTION

An object of the present invention is to provide a novel yellow color forming coupler suitable for use in color photography by a subtractive color process.

Another object of the present invention is to provide a novel yellow color forming coupler which has a high coupling reactivity and with which the dye formation can be completed in a color developer solution.

Another object of the present invention is to provide a novel yellow color forming coupler which forms a dye having excellent spectral absorption properties and fastness to light and humidity.

Still another object of the present invention is to provide a novel yellow color forming coupler in which a coupling off group remains in the molecule of a dye formed and is not leached out from an emulsion layer and thus does not adversely affect the storage of a developer solution.

A further object of the present invention is to provide a method of forming a dye image by developing an exposed silver halide emulsion in the presence of a novel yellow color forming coupler.

A further object of the present invention is to provide a color photographic light-sensitive material having a silver halide emulsion containing a novel yellow color forming coupler.

A still further object of the present invention is to provide a color developer solution containing a novel yellow color forming coupler.

A still further object of the present invention is to provide a color photographic light-sensitive material which is suitable for rapid processing and can form an image having good sharpness.

An even further object of the present invention is to provide a yellow dye image having suitable spectral absorption properties for color reproduction by a subtractive color process and excellent fastness to light and humidity.

These and other objects of the present invention will become apparent from the following detailed description.

These objects of the present invention are accomplished with a yellow color forming coupler represented by the following general formula (I)

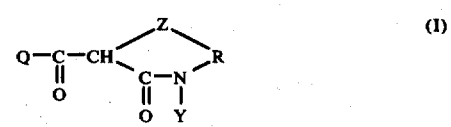

wherein Q represents an aliphatic group, an alicyclic group, an aromatic group or a heterocyclic group; Y represents a hydrogen atom, an aliphatic group, an alicyclic group, an aromatic group or a heterocyclic group; R represents a divalent aliphatic group, a divalent alicyclic group, a divalent aromatic group or a divalent heterocyclic group; and Z represents an oxygen atom, a sulfur atom or a nitrogen atom substituted with an electron attracting group.

DETAILED DESCRIPTION OF THE INVENTION

In the above described general formula (I), suitable groups represented by Q, Y and R include aliphatic groups having 1 to 40 carbon atoms, aromatic groups having 6 to 40 carbon atoms and heterocyclic groups having 3 to 40 carbon atoms.

In greater detail, suitable aliphatic groups represented by Q in the general formula (I) include an alkyl group. The alkyl group can be in the form of a straight chain or a brached chain. The aliphatic group such as a straight chain or branched chain alkyl group, and the alicyclic hydrocarbon group can have up to 20 carbon atoms, which can be substituted with one or more an alkoxy group, e.g., a methoxy, butoxy, octyloxy, decyloxy, etc., group, and aryl group, e.g., a phenyl, tolyl, methoxyphenyl, $\alpha$ or $\beta$-naphthyl, etc., group, an aryloxy group, e.g., a phenoxy, tolyloxy, naphthoxy, etc., group, an amino group, e.g., an amino, an N-alkylamino group such as ethylamino, butylamino, etc., an N-arylamino group such as anilino, methylanilino, etc., group, an acyl group, e.g., an acetyl, butyryl, benzoyl, methylbenzoyl, etc., group, an acylamino group, e.g., an acetamido, butyramido, benzamido, 3-[(2,4-di-tert-amylphenoxy)acetamido]benzamido, etc., group, an alkylthio group, e.g., methylthio, ethylthio, octylthio, dodecylthio, etc., an arylthio group, e.g., phenylthio, tolylthio, α-naphthylthio, etc., a hydroxy group, a halogen atom, e.g., a chlorine, bromine or fluorine atom, and the like. Examples of the aromatic group and the heterocyclic group represented by Q include a phenyl group, a naphthyl group, a pyridyl group, a furyl group, and the like, which can be substituted with one or more of an alkyl group, e.g., a methyl, ethyl, isopropyl, tertbutyl, hexyl, octyl, dodecyl, etc., group, an alkoxy group, e.g., a methoxy, butoxy, octyloxy, decyloxy, etc., group, an aryl group, e.g., a phenyl, tolyl, methoxyphenyl, $\alpha$ or $\beta$-naphthyl, etc., group, an aryloxy group, e.g., a phenoxy, tolyloxy, naphtoxy, etc., group, an acyl group, e.g., an acetyl, butyryl, benzoyl, methylbenzoyl, etc., group, an acylamino group, e.g., an acetamido, butyramido, benzamido, 3-[(2,4-di-tert-amylphenoxy)acetamido]-benzamido, etc., group, a hydroxy group, a carbamoyl group such as a carbamoyl group, an N-alkylcarbamoyl group, e.g., and N-ethylcarbamoyl, N-octadecylcarbamoyl, N-methylcarbamoyl, etc. group, an N-arylcarbamoyl group, e.g., an N-phenylcarbamoyl, 3-pentadecylphenylcarbamoyl, N-{3-[(2,4-di-tert-amylphenoxy)acetamido]phenyl}-carbamoyl, etc., group, an N,N-dialkylcarbamoyl group, e.g., an N-methyl-N-decylcarbamoyl, N,N-dihexylcarbamoyl, N-methyl-N-octadecylcarbamoyl, etc., group, an N-alkyl-N-arylcarbamoyl group, e.g., an N-methyl-N-phenylcarbamoyl, etc., group, an N,N-diarylcarbamoyl group, e.g., an N,N-diphenylcarbamoyl, etc., group, a sulfoamido group, e.g., a methylsulfonamido, butylsulfonamido, benzenesulfonamido, etc., group, a sulfamoyl group such as an N-alkylsulfamoyl group, e.g., an N-methylsulfamoyl, etc., group, an N-arylsulfamoyl group, e.g., an N-phenylsulfamoyl, N-3-[(2,4-di-tert-amylphenoxy))acetamido]phenylsulfamoyl, etc., group, an N,N-dialkylsulfamoyl group, e.g., an N-methyl-N-octadecylsulfamoyl, etc., group, an N-alkyl-N-arylsulfamoyl group, e.g., an N-methyl-N-phenylsulfamoyl, etc., group, an N,N-diarylsulfamoyl group, e.g., an N,N-diphenylsulfamoyl, etc., group, an alkoxycarbonyl group, e.g., a methoxycarbonyl, ethoxycarbonyl, butoxycarbonyl, octadecyloxycarbonyl, etc., group, a halogen atom, e.g., a chlorine, bromine or fluorine atom, and the like.

Z represents an oxygen atom, a sulfur atom or a nitrogen atom, and the nitrogen is susbtituted with an electron attracting group, for example, an acyl group, a sulfonyl group, and the like. Examples of acyl groups include an alkylcarbonyl group having 2 to 10 carbon atoms such as acetyl, propionyl, butyryl, etc., and an arylcarbonyl group such as benzoyl, methylbenzoyl, etc. Examples of sulfonyl groups include an alkylsulfonyl group having 1 to 10 carbon atoms such as methylsulfonyl, ethylsulfonyl, butylsulfonyl, etc. and an arylsulfonyl group such as phenylsulfonyl, tolylsulfonyl, etc. Z is preferably an oxygen atom because of the excellent properties of the resulting coupler.

Examples of aliphatic groups represented by Y and R include an alkyl group. The alkyl group can be in the form of a straight chain or a branched chain. The aliphatic group and the alicyclic group can have up to 20 carbon atoms which can be substituted with one or more of an alkoxy group, e.g., a methoxy, butoxy, octyloxy, decyloxy, etc., group, an aryl group, e.g., a phenyl, tolyl, methoxyphenyl, $\alpha$ or $\beta$-naphthyl, etc., group, an aryloxy group , e.g., a phenoxy, tolyloxy naphthoxy, etc., group, and the like. R represents a divalent group. Representative examples of the aliphatic and alicyclic groups represented by Y and the divalent group represented by R are those described hereinabove for the group Q with the exception that the group R represents a divalent group corresponding to the monovalent group Q.

The term "heterocyclic group" used for the groups Q, Y and R designates a 5-membered or 6-membered heterocyclic ring containing at least one hetero atom selected from the group consisting of a nitrogen atom, an oxygen atom and a sulfur atom and the ring can have a fused ring.

Examples of aromatic groups and heterocyclic groups represented by Y and R include a phenyl group, a naphthyl group, a pyridyl group, a furyl group, and the like, which can be substituted with one or more of a halogen atom, e.g., a chlorine, bromine or fluorine, atom, a nitro group, a cyano group, a thiocyano group, a hydroxy group, an aryloxycarbonylamino group, e.g., a phenyloxycarbonylamino, tolyloxycarbonylamino, etc., group, an alkoxycarbonylamino group, e.g., a methoxycarbonylamino, butoxycarbonylamino, etc., group, an alkylthio group, e.g., methylthio, ethylthio, octylthio, dodecylthio, etc., an arylthio group, e.g., phenylthio, tolylthio, α-naphthylthio, etc., a ureidc group such as alkylureido, e.g., a methylureido, butylureido, etc., group and arylureido, e.g., a phenylureido, tolylureido, etc., group, an alkoxy group, e.g., a methoxy, butoxy, octyloxy, decyloxy, etc., group, an aryloxy group, e.g., a phenoxy, tolyloxy, naphthoxy, etc., group, an alkyl group, e.g., a methyl, ethyl, isopropyl, tert-butyl, hexyl, octyl, dodecyl, etc., group, an alkenyl group, e.g., an allyl, β-vinylethyl, etc., group, an aryl group, e.g., a phenyl, tolyl, methoxyphenyl, $\alpha$ or $\beta$-naphthyl, etc., group, an amino group, e.g., an amino, an N-alkylamino group such as ethylamino, butylamino, etc., an N-arylamino group such as anilino, methylanilino, etc., group, a carboxy group, an acyl group, e.g., an acetyl, butyryl, benzoyl, methylbenzoyl, etc., group, an alkoxycarbonyl group, e.g., a methoxycarbonyl, ethoxycarbonyl, butoxycarbonyl, octadecyloxycarbonyl, etc., group, an aryloxycarbonyl group, e.g., a phenoxycarbonyl, α- or β-naphthoxycarbonyl, tolyloxycarbonyl, etc., group, a sulfonyl group such as an arylsulfonyl, group, e.g., a phenylsulfonyl tolylsulfonyl, etc., group, and an alkylsulfonyl group, e.g., an ethylsulfonyl, dedecylsulfonyl, etc., group, a carbamoyl group such as a carbamoyl group, an N-alkylcarbamoyl group, e.g., an N-ethylcarbamoyl, N-octadecylcarbamoyl, N-methylcarbamoyl, etc., group, an N-arylcarbamoyl group, e.g., an N-phenylcarbamoyl, 3-pentadecylphenylcarbamoyl, N-{3[(2,4-ditert-amylphenoxy)acetamido]phenyl}carbamoyl, etc., group, an N,N-dialkylcarbamoyl group, e.g., an N-methyl-N-decylcarbamoyl, N,N-dihexylcarbamoyl, N-methyl-N-octadecylcarbamoyl, etc., group, an N-alkyl-N-arylcarbamoyl group, e.g., an N-methyl-N-phenylcarbamoyl, etc., group, an N,N-diarylcarbamoyl group, e.g., an N,N-diphenylcarbamoyl, etc., group, an acylamino group, e.g., an acetamido, butyramido, benzamido, 3-[(2,4-di-tert-amylphenoxy)acetamido]benzamido, etc., group, a sulfo group, an alkoxysulfonyl group, an aryloxysulfonyl group, a sulfamoyl group such as an N-alkylsulfamoyl group, e.g., an N-methylsulfamoyl, etc., group, an N-arylsulfamoyl group, e.g., an N-phenylsulfamoyl, N-3-[(2,4-di-tert-amylphenoxy)acetamido]phenylsulfamoyl, etc., group, an N,N-dialkylsulfamoyl group, e.g., an N-methyl-N-octadecylsulfamoyl, etc., group, an N-alkyl-N-arylsulfamoyl group, e.g., an N-methyl-N-phenylsulfamoyl, etc., group, an N,N-diarylsulfamoyl group, e.g., an N,N-diphenylsulfamoyl, etc., group, a sulfonamido group, e.g., a methylsulfonamido, butylsulfonamido, benzenesulfonamido, etc., group, and the like. R represents a divalent group corresponding to the monovalent groups as described above.

Of the yellow color forming couplers according to the present invention, particularly preferred compounds are those represented by the following general formula (II)

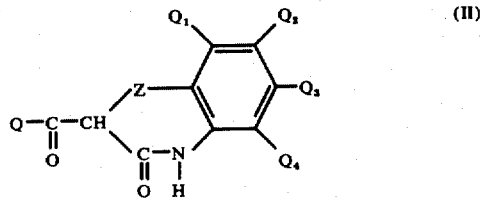

wherein Q and Z are the same as defined in the general formula (I); $Q_1$, $Q_2$, $Q_3$ and $Q_4$, which may be the same or different, each represents a hydrogen atom, a halogen atom (for example, fluorine, chlorine, bromine, etc.), an alkyl group (for example, methyl, trichloromethyl, ethyl, allyl, octadecyl, etc.), an alkoxy group (for example, methoxy, ethoxy, dodecyloxy, etc.), an aryl group (for example, phenyl, chlorophenyl, methylphenyl, etc.), an aryloxy group (for example, phenoxy, methylphenoxy, etc.), an alkoxycarbonyl group (for example, ethoxycarbonyl, hexadecyloxycarbonyl, etc.), a sulfonyl group (for example, alkylsulfonyl such as methylsulfonyl, etc., arylsulfonyl such as penylsulfonyl, p-decyloxyphenylsulfonyl, etc.) a carbamoyl group (for example, alkylcarbamoyl such as methylcarbamoyl, dodecylcarbamoyl, N-ω-(2,4-di-tert-amylphenoxy)butylcarbamoyl, arylcarbamoyl such as phenylsulfamoyl, tolylsulfamoyl, etc.), a sulfamoyl group (for example, alkylsulfamoyl such as methylsulfamoyl, diethylsulfamoyl N-γ-(2,4-di-tert-amylphenoxy)propylsulfamoyl, etc., arylsulfamoyl such as phenylsulfamoyl, tolylsulfamoyl, etc.), an alkylamino group (for example, ethylamino, N,N-dimethylamino, etc.), an arylamino group (for example, anilino, etc.), a sulfoamido group (for example, methylsulfoamido, α-(3-pentadecylphenoxy)propylsulfoamido, etc.), an acylamino group (for example, acetamido, α-(3-pentadecylphenoxy)butyramido, etc.), a carboxy group, a sulfo group, a cyano group, or a hydroxy group.

Methods of forming yellow color images using the photographic couplers of the present invention include an embodiment in which the yellow forming couplers are present in a photographic emulsion layer, and an embodiment in which the yellow color forming couplers are present in a color developer solution. The former is designated a coupler-in-the-emulsion type, and the couplers are usually incorporated in an emulsion layer during the production of the photographic light-sensitive materials. The latter is designated a coupler-in-the-developer type, and the coupler are usually dissolved in a color developer solution and diffuse into an emulsion layer during the color development.

Couplers which can be used in the coupler-in-the-emulsion type preferably are fixed in a specific emulsion layer. That is, these couplers must be diffusion resistant. Otherwise these couplers migrate in the photographic light-sensitive material and form dyes in other emulsion layers of different spectral sensitivity resulting in a marked reduction in the color reproducibility of the photographic materials.

In order to render the couplers diffusion resistant, a group containing a hydrophobic group having at least 8, preferably up to about 32, carbon atoms is preferably introduced into the coupler molecule. Such groups are conventionally designated ballasting groups. The ballasting group can be connected to the coupler skeleton either directly or through an amino bond, an ether bond, a thioether bond, a carbonamido bond, a sulfonamido bond, a ureido bond, an ester bond, an imido bond, a carbonyl bond, a carbamoyl bond, a sulfamoyl bond, a sulfonyl bond, or the like.

In the yellow color foming couplers of the present invention, any of the known ballasting groups can be used. Many ballasting groups are known as described in U.S. Pat. Nos. 2,600,788, 2,865,751, 3,337,344 and 3,418,129, Japanese Patent Publication Nos. 27563/1964 and 19035/1970, Japanese Patent Application Nos. 35379/1973 and 69383/1973, etc., and these can be advantageously employed in the photographic couplers of the present invention. Typical hydrophobic groups include an alkyl group, an alkenyl group, an alkoxyalkyl group, an alkylaryl group, an alkoxyaryl group, and the like, and these groups can be substituted with a halogen atom (such as fluorine, chlorine, etc.), a nitro group, a cyano group, an alkoxycarbonyl group, an amido group, a carbamoyl group, a sulfonamido group, and the like.

Specific examples of ballast groups are illustrated below:

(I). Alkyl groups and alkenyl groups:

(II). Alkoxyalkyl groups:
For instance, $-(CH_2)_3-O-(CH_2)_7CH_3$,
$-(CH_2)_2OCH_2-CH-(CH_2)_6-CH_3$, etc., as described in
              |
              $C_2H_5$
Japanese Patent Publication No. 27563/1964.

For instance, $-CH_2-CH(C_2H_5)_2$, $-C_{12}H_{25}$, $-C_{16}H_{33}$, $-C_{17}H_{35}$, etc.

(III). Alkylaryl groups:
For instance, aryl-$C_9H_{19}$, aryl with $C_4H_9(t)$ and $-C_4H_9(t)$, etc.

(IV). Alkylaryloxyalkyl groups:
For instance, $-CH_2O$-aryl-$C_5H_{11}(t)$,
$-CH_2O$-aryl-$C_5H_{11}(t)$ with $C_2H_5$, $CHO$-aryl-$C_5H_{11}(t)$,
$C_5H_{11}(sec)$, $C_5H_{11}(t)$ with $C_2H_5$,
$-(CH_2)_2O$-aryl-$C_5H_{11}(t)$, $-CHO$-aryl,
$C_5H_{11}(t)$, $C_{16}H_{31}(t)$,
$-CH_2O$-aryl-$C_5H_{11}(t)$ with $C_2H_5$, $-CHO$-aryl with Cl and $C_5H_{11}(t)$,
$CH_3-C-CH_3$
    |
    $CH_2-C_4H_9(t)$
$C_5H_{11}(t)$
etc.

(V). Acylamidoalkyl groups:
For instance, $-CH_2CH_2N\begin{smallmatrix}COC_{15}H_{31}\\C_4H_9\end{smallmatrix}$,
$-CH_2CH_2N\begin{smallmatrix}COC_{12}H_{27}\\C_3H_7\end{smallmatrix}$, $-CH_2CH_2NHCOCH_2CH_2N\begin{smallmatrix}COC_{12}H_{27}\\C_3H_7\end{smallmatrix}$ as described in U.S. Pat. No. 3,337,344 and 3,418,129.

(VI). Alkoxyaryl groups and aryloxyaryl groups:
For instance, aryl-$OC_{12}H_{27}(n)$,
aryl-O-aryl-$C_{12}H_{25}(n)$, etc.

(VII). Residues having a long chain alkyl or alkenyl aliphatic group and also carboxyl or sulfo water-solubilizing group:
For instance, $-CH-CH=CH-C_{16}H_{33}$, $-CH-C_{16}H_{33}$,
              |                         |
              $CH_2COOH$                $SO_3H$
etc.

(VIII). Alkyl groups substituted with an ester group:
For instance, $-CH-C_{16}H_{33}(n)$,
              |
              $COOC_2H_5$
$-CH_2-CH_2-COOC_{12}H_{25}(n)$, etc.

(IX). Alkyl groups substituted with an aryl group or a heterocyclic group:
For instance,
$-CH_2-CH_2$-aryl-$NHCOCH_2CH-C_{16}H_{37}(n)$,
                                |
                                $COOCH_3$ $-CH_2CH_2$-aryl-N(C=O)(C=O)$C_{16}H_{37}(n)$, etc.

(X). Aryl groups substituted with an aryloxyalkoxy-carbonyl group:
For instance, aryl-$COOCH_2CHO$-aryl-$C_5H_{11}(t)$, etc.
              |           with $C_5H_{11}(t)$
              $C_2H_5$ A coupler having diffusion resistant group in the molecule can be dissolved in an organic solvent and incorporated into an photographic emulsion as fine particles in a conventional manner. An example of a method of dispersion the couplers which is particularly suitable in the practice of the present invention is described in detail in U.S. Pat. No. 3,676,137. Organic solvents which can be used to dissolve the coupler are described in U.S. Pat. Nos. 2,322,027, 3,253,291, 3,574,627, etc. These solvents include those which are sparingly soluble in water and have a high boiling point (higher than about 170° C) and remain in a color photographic light-sensitive material together with the couplers, for example, substituted hydrocarbons, carboxylic acid esters, carboxylic acid amides, phosphoric acid esters, ethers, and the like. Specific examples of these solvents are di-n-butyl phthalate, di-isooctyl azelate, di-n-butyl sebacate, tricresyl phosphate, tri-n-hexyl phosphate, N,N-diethylcaprylamide, butyl-m-pentadecyl phenyl ether, chlorinated paraffin, and the like. An auxiliary solvent which can be removed during the production of the photographic light-sensitive material can be advantageously used in combination with the high boiling solvent to facilitate the dissolution of the coupler. Examples of such solvents are propylene carbonate, ethyl acetate, butyl acetate, cyclohexanol, ethyl tetrahydrofuran, cyclohexanone, and the like.

To facilitate the formation of a fine dispersion of the oil-soluble couplers in a hydrophilic high molecular weight material which is used in a photographic emulsion, a surface active agent can be advantageously used. Particularly, an anionic surface active agent such as sodium cetylsulfate, sodium p-dodecylbenzene sulfonate, sodium nonylnaphthalene sulfonate, sodium di(2-ethylhexyl)-α-sulfosuccinate, and the like, and a nonionic surface active agent such as sorbitan sesquioleate, sorbitan monolaurate, and the like are suitable. An emulsifying device such as a homogenizer, a colloid mill, an ultrasonic wave emulsifier, and the like is preferably used to prepare a dispersion of an oil-soluble coupler.

The diffusion resistant coupler which contains both a ballasting group and a carboxylic acid group or a sulfonic acid group is soluble in a neutral or weakly alkaline aqueous solution. By addition of an aqueous solution of the coupler to a photographic emulsion, the coupler can be incorporated into the photographic emulsion. It is believed that the coupler is rendered diffusion resistant in a micellar form in the hydrophilic high molecular weight material.

A diffusible coupler which does not contain a diffusion resistant group can be used by addition to a color developer solution containing an aromatic primary amine color developing agent.

Representative examples of yellow color forming couplers represented by the general formula (I) are illustrated below.

(1) 2-Pivaloyl-6-(4-decyloxyphenylsulfonyl)benzomorpholone
(2) 2-Pivaloyl-6-[γ-(2,4-di-tert-pentylophenoxy)-propylcarbamoyl]- benzomorpholone
(3) 2-Pivaloyl-6-dodecyloxycarbonylbenzomorpholone
(4) 2-Pivaloyl-6-dodecyloxycarbonyl-1-thiabenzomorpholone
(5) 2-(4-Methoxybenzoyl)-6-(4-decyloxyphenylsulfonyl)benzomorpholone
(6) 2-Benzoyl-6-methyl-7-[γ(2,4-di-tert-pentylphenoxy)- propylsulfamoyl]benzomorpholone
(7) 2-(4-Methoxybenzoyl)-6-dodecyloxycarbonylbenzomorpholone
(8) 2-(-Methyl-2-ethylthiopropionyl)-6-(4-decyloxyphenylsulfonyl) benzomorpholone
(9) 2-(2-Methyl-2-octylthiopropionyl)-6-carboxybenzomorpholone
(10) 2-(2-Methyl-2-octadecylthiopropionyl)-6-trifluoromethylbenzomorpholone
(11) 1-Perfluorobutyrl-2-(2-methyl-2-ethoxypropionyl)-3-oxo- 1,2,3,4-tetrahydroquinoxaline
(12) 1-[γ-(3-Pentadecylphenoxy)propysulfonyl]-2-pivaloyl-3- oxo-1,2,3,4-tetrahydroquinoxaline
(13) 2-{3-[α-(2,4,-Di-tert-pentylphenoxy)- butyramido]benzoyl}-6- carboxybenzomorpholone
(14) 2-Pivaloyl-6-[γ-(2,4-di-tert-pentylphenoxy)-butyramido]- benzomorpholone
(15) 2-Pivaloyl-6-[α-(2,4-di-tert-pentyphenoxy)-butyramido]- benzomorpholone
(16) 2-(2-Methyl-2-octylthiopropinoyl-5-ethoxycarbonylbenzomorpholone
(17) 1-Pivaloyl-6-nitrobenzomorpholone
(18) 2-(2-Methyl-2-diethylaminopropionyl)-6-(4-decyloxyphenyl- sulfonyl) benzomorpholone
(19) 2-[2-Methyl-2-(3-pentadecylphenoxy)propionyl]-6-octafluorobutylsulfonamidobenzomorphone
(20) 2-(2-Methyl-2-ethylthiopropionyl-6-dodecyloxycarbonylbenzomorpholone The yellow color forming coupler represented by the general formula (I) of the present invention can be easily prepared in high yield according to a synthesis route shown schematically below

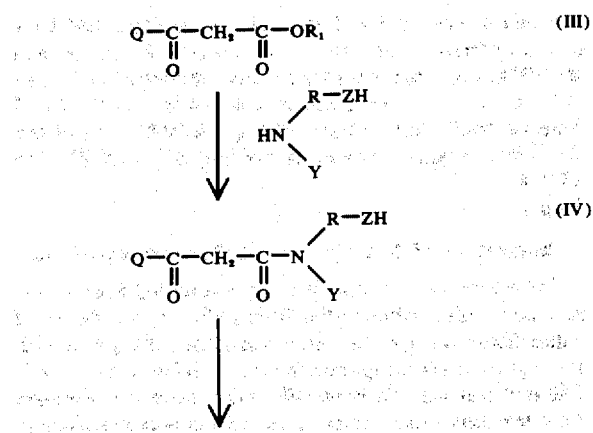

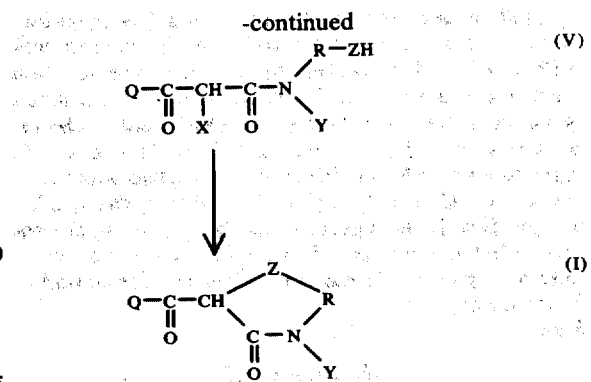

wherein $R_1$ represents an alkyl group or an aryl group; X represents a halogen atom; and Q, Y, R and Z each has the same meaning as defined in general formula (I).

Although the ring closing reaction is carried out at the final step in the above described synthesis route, the ring closing reaction can be carried out initially and then a group having a ballasting group can be introduced into the structure, if desired.

The compound represented by the general formula (IV) can be easily prepared by condensing the compound of the general formula (III) and the compound of the formula

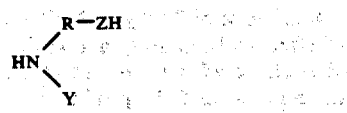

using known methods, for example, the method described in U.S. Pat. No. 3,265,506, etc.

The compound represented by the general formula (V) can be easily prepared using a conventional method in which the compound of the general formula (IV) is reacted with a halogenating agent such as a halogen atom, sulfuryl chloride, etc. in a solvent such as chloroform, carbon tetrachloride, acetic acid, diethyl either, etc. at a temperature of 0° to 100° C for a period from 1 minute to 10 hours.

The yellow color forming coupler represented by the general formula (I) of the present invention can be prepared with ease and in high yield by a method comprising reacting the compound of the general formula (V) with an alkali such as an alkali metal carbonate, an alkali metal hydroxide, an alkali metal alkoxide, etc. in an appropriate solvent such as dimethylformamide, dimethylsulfoxide, ethanol, etc.

Specific examples of the synthesis of the compounds of this invention are illustrated below. Unless otherwise indicated, all parts, percents, ratios and the like are by weight.

SYNTHESIS EXAMPLE 1

Preparation of 2-Pivaloyl-6-(4-decyloxyphenylsulfonyl)-benzomorpholone (Coupler 1)

Step 1

Preparation of 4-Hydroxy-4'-decyloxydiphenylsulfone

A mixture of 130 g of 4,4'-dihydroxydiphenylsulfone, 35 g of sodium ethoxide and 700 ml of ethanol was refluxed by heating and 114 g of decylbromide was generally added dropwise thereto over a 3 hour period. After the completion of the addition, the mixture was further refluxed by heating for 2 hours. The reaction mixture was poured into 2 liters of water and extracted twice, each time with 500 ml of ethyl acetate. The extract was washed twice, each time with 500 of a 10% aqueous sodium hydroxide solution, washed with water and dried. After distilling off the solvent, the residue was purified by silica gel chromatography using chloroform-ethyl acetate (10:1 in volume) as a developer to obtain 64 g (yield 31.6%) of the desired compound as a viscous oil.

Step 2

Preparation of 3-Nitro-4-hydroxy-4'-decyloxydiphenylsulfone

A solution of 190 g of 4-hydroxy-4'decyloxydiphenylsulfone obtained in Step 1 above and 1 liter of glacial acetic acid was heated at 60° C and to which 23 ml of fuming nitric acid was gradually added dropwise over a 1 hour period. After the completion of the addition, the mixture was further stirred for 1 hour at 60° C. By cooling the reaction mixture to 15° C, pale yellow crystals of the desired compound were deposited. Yield: 160 g (75%). Melting Point: 107° to 108° C Step 3

Preparation of 3-Amino-4-hydroxy-4'-decyloxydiphenylsulfone

A mixture of 22.8 g of 3-nitro-4-hydroxy-4'-decyloxydiphenylsulfone obtained in Step 2 above and 200 ml of acetic acid was heated at 70° C under a nitrogen atmosphere and 30 g of reducing iron was gradually added thereto over an about 10 minute period with stirring. The reaction was filtered and the filtrate was poured into 500 ml of ice water and the deposited crystals were collected. Yield: 20 g (95%). The melting point of the crystals after recrystallization from a solvent mixture of ethanol and water (1:1 in volume) was 196° to 199° C.

Step 4

Preparation of α-Pivaloyl-2-hydroxy-5-(4-decyloxyphenyl-sulfonyl)acetanilide A mixture of 17.5 g of 3-amino-4-hydroxy-4'-decyloxydi-phenylsulfone obtained in Step 3 above, 5.3 g of ethyl pivaloylacetate and 50 ml of xylene was refluxed by heating for 6 hours. Xylene was distilled off from the reaction mixture and the residue was recrystallized from acetonitrile to obtain 17.2 g (yield 83%) of the desired compound. Melting Point: 70° to 76° C Step 5

Preparation of 2-Pivaloyl-6-(4-decyloxyphenlsulfonyl)-benzmorpholone

To a mixture of 9 g of α-pivaloyl-2-hydroxy-5-(4-decyloxyphenylsulfonyl) acetanilide obtained in Step 4 above and 200 ml of chloroform, a solution of 3.2 g of bromine and 30 ml of chloroform was added with stirring under cooling with an ice bath over a 30 minute period. The reactions mixture was poured into 200 ml of ice water. The chloroform layer was sufficiently washed with water. To the chloroform solution containing α-pivaloyl-α-bromo-2-hydroxy- 5-(4-decyloxyphenylsulfonyl)acetanilide as a main component, 10 ml of dimethylformamide and a solution containing 1.5 g of potassium hydroxide dissolved in 50 ml of methanol were added and the mixture was stirred for 1 hour at room temperature (about 20°–30° C). The reaction mixture was sufficiently washed with water and dried. After distilling off the solvent, the residue was recrystallized from acetonitrile to obtain 6.4 g (yield 67%) of the desired coupler. Melting Point: 157° to 160° C Elemental Analysis: Calculated for $C_{29}H_{39}NO_6S$ (%): C: 65.78, H: 7.37, N: 2.65; Founded (%): C: 65.71, H: 7.20, N: 2.71.

SYNTHESIS EXAMPLE 2

Preparation of 2-(2-Methyl-2-octylthiopropionyl)-5-ethoxycarbonyl-benzomorpholone (Coupler 16)

Step 1

Preparation of α-(2-Methyl-2-octylthiopropionyl)-2-hydroxy-5-ethoxycarbonylacetanilide A mixture of 55 g of ethyl 2-methyl-2-octylthiopropionylacetate (boiling point: 140° to 144° C/0.3 mm Hg) prepared by the method described in Japanese Patent Application No. 37239/1974 and 33 g of ethyl 3-amino-4-hydroxybenzoate was stirred in an oil bath at 150° C for 3 hours under a reduced pressure of 50 to 100 mm Hg. The reaction mixture was recrystallized from acetonitrile to obtain 48 g (yield 60.4%) of the desired compound having a melting point of 100 to 101° C.

Step 1:

Preparation of 2-(2-Methyl-2-octylthiopropionyl)-5-ethoxycarbonyl-benzomorpholone The same procedures as described in Step 5 of Synthesis Example 1 were carried out but using 8.2 g of α-(2-methyl-2-octylthiopropionyl) -2-hydroxy-5-ethoxycarbonylacetanilide obtained in Step 1 above to obtain 5.1 g (yield 62.4%) of the desired compound having a melting point of 93° to 94° C.

Elemental Analysis:

Calculated for $C_{23}H_{35}NO_5S$ (%): C: 63.44, H: 7.58, N: 3.21; Found (%): C: 63.63, H: 7.74, N: 3.48.

SYNTHESIS EXAMPLE 3

Preparation of 2-Pivaloyl-6-nitrobenzomorpholone (Coupler 17)

Step 1

Preparation of α-Pivaloyl-2-hydroxy-5-nitroacetanilide

A mixture of 17.2 g of ethyl pivaloylacetate and 15.4 g of 2-hydroxy-5-nitroaniline was stirred in an oil bath at 150° C for 3 hours under a reduced pressure of 50 to 100 mm Hg. The reaction mixture was recrystallized from acetonitrile to obtain 18.9 g (yield 67.5%) of the desired compound having a melting point of 231° to 232° C.

Step 2

Preparation of 2-Pivaloyl-6-nitrobenzomorpholone

To a mixture of 8.4 g of α-pivaloyl-2-hydroxy-5-nitroacetanilide obtained in Step 1 above and 500 ml of chloroform, 4.8 g of bromine was added dropwise with stirring at room temperature over a 30 minute period. Chloroform was distilled off under reduced pressure from the reaction mixture. The residue was dissolved in 50 ml of dimethylformamide and a solution containing 1.0 g of potassium hydroxide dissolved in 50 ml of methanol was added thereto with stirring at room temperature over a 5 minute period. After stirring for 30 minutes, the reaction mixture was poured into 200 ml of ice water and extracted with 500 ml of methyl acetate. The extract was washed with water and dried. After distilling off the solvent, the residue was recrystallized from ethanol to obtain 4.9 g (yield 58.8%) of the desired compound having a melting point of 158° to 160° C.

Elemental Analysis: Calculated for $C_{13}H_{14}O_5N_2$ (%): C: 56.11, H: 5.03, N: 10.07 Found (%): C: 56.18, H: 5.09, N: 10.06.

SYNTHESIS EXAMPLE 4

Preparation of 2-Pivaloyl-6-[γ-(2,4-di-tert-pentylphenoxy)-butyramido]benzomorpholone (Coupler 14)

A mixture of 2.7 g of 2-pivaloyl-6-nitrobenzomorpholone obtained in Synthesis Example 3 and 50 ml of acetic acid was heated at 80° under a nitrogen atmosphere and 3 g of reducing iron was added thereto with stirring. After heating and stirring for 5 minutes the mixture was cooled to room temperature. The reaction mixture contained almost pure 2-pivaloyl-6-aminobenzomorpholone. To the reaction mixture, 1 g of sodium acetate and then 4 g of γ-(2,4-di-tert-pentylphenoxy)-butyl chloride were added and the mixture was stirred at room temperature for 1 hour. The reaction mixture was poured into 200 ml of ice water and extracted with 300 ml of ethyl acetate. After washing with water, drying and distilling off the solvent, the residue was recrystallized from acetonitrile to obtain 2.8 g (yield 51%) of the desired compound having a melting point of 203 to 203.5° C. Elemental Analysis:

Calculated for $C_{33}H_{46}N_2O_5$ (%): C: 72.00, H: 8.36, N: 5.09; Found (%): C: 72.24, H: 8.50, N: 5.21.

SYNTHESIS EXAMPLE 5

Preparation of 2-Pivaloyl-6-[α-(2,4,-di-tert-pentylphenoxy)-butyramido]benzomorpholone (Coupler 15)

2-Pivaloyl-6-aminobenzomorpholone was obtained in the same manner as described in Synthesis Example 4 using 2-pivaloyl-6-nitrobenzomorpholone obtained in Synthesis Example 3. Then α-(2,4-di-tert-pentylphenoxy)butyl chloride was reacted with the 2-pivaloyl-6-aminobenzomorpholone using the same procedures described in Synthesis Example 4 to obtain the desired compound having a melting point of 103° to 105° C. Yield: 59% Elemental Analysis:

Calculated for $C_{33}H_{46}N_2O_5$(%): C: 72.00, H: 8.36, N: 5.09; Found (%): C: 72.15, H: 8.40, N: 5.11.

SYNTHESIS EXAMPLE 6

Preparation of 2-Pivaloyl-6-dodecyloxycarbonylbenzomorpholone (Coupler 3)

Step 1

Preparation of Dodecyl 3-Nitro-4-hydroxybenzoate

A solution of 10 g of dodecyl 4-hydroxybenzoate and 60 ml of acetic acid was heated at 30° to 35° C and a solution of 2 ml of fuming nitric acid and 10 ml of acetic acid was added dropwise thereto over a 20 minute period with stirring. After the completion of the addition, the mixture was stirred for 1 hour. The crystals deposited in the reaction mixture were collected by filtration, washed with water and recrystallized from ethanol to obtain 11.0 g (yield 95.8%) of the desired compound having a melting point of 70° C.

Step 2

Preparation of Dodecyl 3-Amino-4hydroxybenzoate

A mixture of 10.5 g of dodecyl 3-nitor-4-hydroxybenzoate obtained in Step 1 above and 100 ml of acetic acid was heated at 70° C under a nitrogen atmosphere and 10 g of reducing iron was added thereto over a 5 minute period with stirring. The reaction mixture was filtered and the filtrate was poured into 500 ml of ice water to deposit the crystals. The crystals were washed and dried to obtain 8.2 g (yield 85%) of the desired compound having a melting point of 86° to 89° C.

Step 3

Preparation of α-Pivaloyl-2-hydroxy-5-dodecyloxycarbonyl-acetanilide

A mixture of 20 g of dodecyl 3-amino-4-hydroxybenzoate obtained in Step 2 above and 13 g of ethyl pivaloylacetate was stirred in an oil bath at 140° C under a reduced pressure of 50 to 100 mm Hg for 2 hours. The reaction mixture was crystallized from hexane to obtain 25 g (yield 72%) of the desired compound having a melting point of 93 to 95° C.

Step 4

Preparation of 2-Pivaloyl-6-dodecyloxycarbonylbenzomorpholone

To a mixture of 3.5 g of α-pivaloyl-2-hydroxy-5-dodecyloxycarbonylacetanilide obtained in Step 3 above and 50 ml of chloroform in an ice bath, a solution of 1.6 g of bromine and 30 ml of chloroform was added dropwide over a 20 minute period with stirring. After the completion of the addition, the reaction mixture was sufficiently washed with water and 300 ml of dimethylformamie and a solution of 0.7 g sodium hydroxide dissolved in 30 ml of methanol were added thereto and the mixture was stirred at room temperature for 1 hour. The reaction mixture was poured into 3 liters of water and the chloroform layer was sufficiently washed with water. After drying and distilling off the solvent, the residue was recrystallized from hexane to obtain 2.5 g (yield 72.5% ) of the desired compound having a melting point of 77 to 78° C. Elemental Analysis:

Calculated for $C_{26}H_{39}NO_5$(%): C: 70.11, H: 8.76, N: 3.15; Found (%): C: 69.89, H: 8.81, N: 3.01.

SYNTHESIS EXAMPLE 7

Preparation of 2-(2-Methyl-2-ethylthiopropionyl)-6-dodecyloxycarbonylbenzomorpholone (Coupler 20)

Step 1

Preparation of α-(2-Methyl-2-ethylthiopropionyl)-2-hydroxy-5-dodecyloxycarbonylacetanilide A mixture of 32.1 g of dodecyl 3-amino-4-hydroxybenzoate obtained in Step 2 of Synthesis Example 6 and 21.8 g of ethyl 2-methyl-2-ethylthiopropionylacetate prepared by the method described in Japanese Patent Application No. 37239/1974 was stirred in an oil bath at 150° C under a reduced pressure of 50 to 100 mm Hg for 3 hours. The reaction mixture was recrystallized from hexane to obtain 35 g (yield 71%) of the desired compound having a melting point of 89° to 90° C.

Step 2

Preparation of
2-(2-Methyl-2ethylthiopropionyl)-6-dodecyloxycarbonylbenzomorpholone The same procedures as described in Step 4 of Synthesis Example 6 were carried out but using α-(2-methyl-2-ethylthiopropionyl)-2-hydroxy-5-dodecyloxycarbonylacetanilide obtained in Step 1 above to obtain the desired compound having a melting point of 85° to 86° C. Yield: 59%

Elemental Analysis: Calculated for $C_{27}H_{41}NO_5S$ (%): C: 65.99, H: 8.35, N: 2.85; Found (%): C: 65.80, H: 8.39, N: 2.99.

The yellow color forming coupler of the present invention represented by the general formula (I) can be used individually or as a combination of two or more. Also the yellow color forming coupler of the present invention can be used together with one or more couplers other than the couplers represented by the general formula (I). Examples of these other couplers which can be used include four-equivalent or two-equivalent diketomethylene type yellow color forming couplers such as those described, for example, in U.S. Pat. Nos. 3,277,155; 3,415,652; 3,447,928; 3,408,194; 2,875,057; 3,265,506; 3,409,439; 3,551,155; 3,551,156 and 3,582,322; Japanese Patent Application (OPI) Nos. 26133/1972; 66834/1973; 66835/1973 and 66836/1973; four-equivalent or two-equivalent pyrazolone or indazolone type magenta color forming couplers such as those described, for example, in U.S. Pat. Nos. 2,600,788; 2,983,608; 3,006,759; 3,062,653; 3,214,437; 3,253,924; 3,311,476; 3,419,391; 3,419,803; 3,476,560 and 3,582,322; Japanese Patent Publication No. 20636/1970; Japanese Patent Application (OPI) No. 26133/1972; four-equivalent or two-equivalent α-naphthol or phenol type cyan color forming couplers such as those described, for example, in U.S. Pat. Nos. 2,474,293; 2,698,794; 3,034,892; 3,214,437; 3,253,924; 3,311,675; 3,458,315; 3,582,322 and 3,591,383; Japanese Patent Publication No. 11304/1967 and 32451/1969. In addition, DIR couplers such as those described, for example, in U.S. Pat. Nos. 3,227,544; 3,297,445; 3,253,924; 3,311,476; 3,379,529; 3,516,831; 3,617,291 and 3,705,801; German Patent Application (OLS) No. 2,163,811, can also be used.

The couplers can be incorporated into a photographic material using the methods as described in U.S. Pat. Nos. 2,322,027 and 2,801,171, and the like.

The couplers of the present invention and other couplers can be incorporated into the same or different silver halide emulsion layers or adjacent layers thereof or other layers.

The amount of the coupler employed in the present invention can be varied depending on the type of photographic light-sensitive material and the processing employed. In the case of a coupler-in-the-emulsion type material, a range of from about 0.02 to about 1 mole per mole of silver halide in the emulsion layer is particularly preferred. If the amount incorporated is excessively less than about 0.20 mole, a large amount of silver halide is required to provide the desired color density, and thus the light-scattering in the emulsion layer tends to increase, which results in a reduction in the sharpness of the images formed. The increase in the amount of silver coated also leads to an increase in the thickness of the emulsion layer resulting in an increase in the time required for processing. On the other hand, if the amount incorporated is excessively more than about 1 mole, couplers which are not converted to dyes by color development remain in the emulsion layer and the efficiency of coupler utilization is reduced. This is disadvantageous from an economical standpoint and results in an increase in the thickness of the emulsion layer accompanied by the above-described disadvantages. When the coupler of the present invention is used outside the above-described range, the advantages which can be achieved by the present invention may not be obtained sufficiently.

Where the coupler is employed in the developer, a range from about 0.2 to about 50 g of the coupler per 1000 ml of the color developer, solution is useful. If the amount added is excessively less than about 0.2 g, the above-described disadvantages are encountered. On the other hand, if the amount added is excessively more than about 50 g, disadvantages exist in that a large amount of a water-miscible organic solvent must be employed in order to dissolve the coupler into a color developer solution and in that a large amount of alkali is necessary when preparing the color developer solution, in addition to the above-described disadvantages. A particularly preferred amount of the coupler employed in the developer ranges from 0.5 to 10 g per 1000 ml of the color developer solution.

Furthermore, the couplers according to the present invention can also be used in a photographic light-sensitive material which contains a low amount of silver halide in an extent of about one half to one hundredth in comparison with a conventional photographic light-sensitive material. These color photographic light-sensitive materials containing a small amount of silver halide provide color images of sufficiently high density using a method in which developed silver formed by color development is halogenation-bleached and then color developed again to increase the amount of dye formed, such as described, for example, in U.S. Pat. Nos. 2,623,822 and 2,824,565, or using a method for increasing the amount of dye formed with a color intensification method using a peroxide or a cobalt complex salt as described, for example, in German Patent Application (OLS) No. 2,357,694, U.S. Pat. Nos. 3,674,490 and 3,761,265, German Patent Application (OLS) Nos. 2,044,833, 2,056,359, 2,056,360 and 2,226,770 and Japanese Patent Application (OPI) Nos. 9728/1973 and 9729/1973.

The silver halide photographic emulsion which can be used in the present invention comprises a light-sensitive silver halide such as silver chloride, silver bromide, silver chlorobromide, silver chloroiodide, silver iodobromide, silver chloroiodobromide, etc., dispersed in a hydrophilic high molecular weight material, and it can be prepared by various methods. Suitable hydrophilic high molecular weight materials present in the photographic emulsion include proteins such as gelatin, etc., high molecular weight nonelectrolytes such as polyvinyl alcohol, polyvinyl pyrrolidone, polyacrylamide, etc., high molecular weight amphoteric materials such as a polyacrylamide treated with the Hoffman reaction, a copolymer of acrylic acid and N-vinylimidazole, etc. The silver halide photographic emulsion can also contain various additives which are added to conventional color photographic silver halide emulsions, such as a chemical sensitizing agent, a stabilizer, an antifogging agent, a hardening agent, a spectral sensitizing dye, a surface active agent, and the like.

Examples of suitable chemical sensitizing agents include, for example, gold compounds such as chloroaurates and gold trichloride as described in U.S. Pat. Nos. 2,399,083; 2,540,085; 2,597,856 and 2,597,915; salts of a noble metal, such as platinum, palladium, iridium, rhodium and ruthenium, as described in U.S. Pat. Nos. 2,448,060; 2,540,086; 2,566,245; 2,566,263 and 2,598,079; sulfur compounds capable of forming silver sulfide by reacting with a silver salt, such as those described in U.S. Pat. Nos. 1,574,944; 2,410,689; 3,189,458 and 3,501,313; stannous salts, amines and other reducing compounds such as those described in U.S. Pat. Nos. 2,487,850; 2,518,698; 2,521,925; 2,521,926; 2,694,637; 3,983,610 and 3,201,254, and the like.

Examples of suitable stabilizers or antifogging agents include a wide variety of known compounds such as, for example, heterocyclic compounds, mercury-containing compounds, mercapto compounds or metal salts, including 4-hydroxy-6-methyl-1,3,3a, 7-tetraazaindene, 3-methylbenzothiazole and 1-phenyl-5-mercaptotetrazole. Other examples of such compounds are described, for example, in U.S. Pat. Nos. 1,758,576; 2,110,178; 2,131,038; 2,173,628; 2,697,040; 2,304,962; 2,324,123; 2,394,198; 2,444,605-8; 2,566,245; 2,694,716; 2,697,099; 2,708,162; 2,728,663-5; 2,476,536 2,824,001; 2,843,491; 2,886,437; 3,052,544; 3,137,577; 3,220,839; 3,226,231; 3,236,652; 3,251,691; 3,252,799; 3,287,135; 3,326,681; 3,420,668 and 3,622,339; and British Patent Nos. 893,428; 403,789; 1,173,609 and 1,200,188; as well as in C.E.K. Mees & T. H. James, *The Theory of the Photographic Process*, 3rd Ed. Macmillan, New York (1966) and the literature references cited therein.

Examples of suitable hardeners include, for example, an aldehyde compound such as formaldehyde and glutaraldehyde; a ketone compound such as diacetyl and cyclopentadione; a reactive halogen-containing compound such as bis(2-chloro-ethylurea), 2-hydroxy-4,6-dichloro-1,3,5-triazine and those described in U.S. Pat. Nos. 3,288,775 and 2,732,303; and British Patent Nos. 974,723 and 1,167,207 a reactive olefin-containing compound such as divinyl sulfone, 5-acetyl-1,3-diacryloylhexahydro-1,3,5-triazine and those described in U.S. Pat. Nos. 3,635,718 and 3,232,763; and British Patent No. 994,869; an N-methylol compound such as N-hydroxymethylphthalimide and those described in U.S. Pat. Nos. 2,732,316 and 2,586,168; an isocyanate compound such as those described in U.S. Pat. No. 3,103,437; an aziridine compound such as those described in U.S. Pat. Nos. 3,017,280 and 2,983,611; an acid derivative such as those described in U.S. Pat. Nos. 2,725,294 and 2,725,295; a carbodiimide compound such as those described in U.S. Pat. No. 3,100,704; an epoxy compound such as those described in U.S. Pat. No. 3,091,537; an isooxazole type compound such as those described in U.S. Pat. Nos. 3,321,313 and 3,543,292; a halocarboxyaldehyde such as mucochloric acid; a dioxane derivative such as dihydroxydioxane and dichlorodioxane; and an inorganic hardner such as chrome alum and zirconium sulfate. Instead of the above compounds, precursors of hardeners such as alkali metal bisulfite-aldehyde adducts, methylol derivatives of hydantoin, primary fatty nitroalcohols and the like can also be used.

Suitable spectral sensitizing dyes which can be used include a cyanine dye such as a cyanine, a merocyanine and a carbocyanine. These cyanine dyes can be used individually or in combination. Further, spectral sensitization techniques using a combination of a cyanine dye and a styryl dye can also be employed. Examples of suitable spectral sensitizing dyes are described, for example, in U.S. Pat. Nos. 2,493,748; 2,519,001; 2,977,229; 3,480,434; 3,672,897; 3,703,377; 2,688,545; 2,912,329; 3,397,060; 3,615,635 and 3,628,964; British Patent Nos. 1,195,302; 1,242,588 and 1,293,862; German Patent Application (OLS) Nos. 2,030,326 and 2,121,780; Japanese Patent Publication Nos. 4936/1968; 14030/1969 and 10773/1968; U.S. Pat. Nos. 3,511,664; 3,522,052; 3,527,641; 3,615,613; 3,615,632; 3,617,295; 3,635,721 and 3,694,217; and British Patent Nos. 1,137,580 and 1,216,203 and the like. The sensitizers can be chosen as desired depending on the spectral range, sensitivity, etc., based on the purposes and uses of the photographic materials to be sensitized.

A surface active agent can be used inidvidually or in combination. The surface active agents are commonly used as a coating aid. However, in some cases they are used for the purpose of emulsifying, dispersing, sensitizing, improving photographic properties, antistatic characteristics, adhesion preventing, or the like.

The surface active agents can be classified as natural surface active agents such as saponin; nonionic surface active agents such as alkylene oxides, glycerols and glycidols; cationic surface active agents such as higher alkylamines, quaternary ammonium salts, heterocyclic compounds such as pyridien and the like, phosphoniums or sulfoniums; anionic surface active agents containing an acid group such as a carboxylic acid group, a sulfonic acid group, a phosphoric acid group, a sulfuric acid ester group, or a phosphoric acid ester group; amphoteric surface active agents such as amino acids, aminosulfonic acids, aminoalcohol sulfuric acid esters or amino alcohol phosphoric acid esters. Some examples of those surface active agents which can be used are described, for example, in U.S. Pat. Nos. 2,271,623; 2,240,472; 2,288,226; 2,739,891; 3,068,101; 3,158,484; 3,201,253; 3,210,191; 3,294,540; 3,415,649; 3,441,413; 3,442,654; 3,475,174; 3,545,974; German Patent Application (OLS) No. 1,942,665; and British Patent Nos. 1,077,317 and 1,198,450 as well as in Ryohei Oda et al, *Kaimenkasseizai no Gosei to sono Oyo* (*Synthesis and Applications of Surface Active Agents*), Maki Shoten (1964); A. M. Schwartz, *Surface Active Agents*, Interscience Publications Inc. (1958) and J. P. Sisley, *Encyclopedia of Surface Active Agents*, Vol. II. Chemical Publishing Co. (1964).

The photographic emulsion can be applied to a sustantially planar material which does not undergo severe dimensional change during processings, for example, a rigid support such as glass, metal or ceramics, or a flexible support as desired. Representative flexible supports include those generally employed for photographic materials, such as a cellulose nitrate film, a cellulose acetate film, a cellulose acetate butyrate film, a cellulose acetate propionate film, a polystyrene film, a polyethylene terephthalate film, a polycarbonate film, a laminate of these polymers, a thin glass film and a paper. A baryta coated paper, a paper which is coated or laminated with an α-olefin polymer, particularly those obtained from an olefin monomer having from 2 to 10 carbon atoms, such as polyethylene, polypropylene and ethylene-butene copolymers, and a synthetic resin film in which the adhesiveness to other polymers and the printing properties are improved by roughening the surfaces thereof, such as described in Japanese Patent Publication No. 19068/1972, can also be used to advantage as a support.

These supports can be transparent or opaque, depending on the purposes of the photographic materials. Colored transparent supports which contain a dye or pigment can also be used. Such colored supports have been utilized in X-ray films, and are described in *J. SMPTE*, Vol. 67, Page 296 (1958).

Examples of opaque supports include opaque films produced by incorporating into a transparent film a dye or a pigment such as titanium oxide and zinc oxide, or surface-treated synthetic resin films such as those described in Japanese Patent Publication No. 19068/1972, as well as intrinsically opaque materials such as paper. Highly light-shielding papers and synthetic resin films containing, for example, carbon black or dyes can also be used. When the adhesion between a support and a photographic layer is unsatisfactory, a subbing layer which adheres to both of the support and the photographic layer can be provided on the support. The surfaces of the supports can also be pre-treated with a corona discharge, a UV radiation treatment, a flame treatment and the like in order to further improve the adhesiveness.

The photographic layers can be coated on a support using various conventional coating methods, including, for example, a dip coating method, an air-knife coating method, a curtain coating method and an extrusion-coating method using the hopper described in U.S. Pat. No. 2,81,294. If desired, two or more layers can be coated simultanously using the methods as described in U.S. Pat. Nos. 2,761,791; 3,508,947; 2,941,898 and 3,526,528. Generally, the silver halide is coated in an amount of about $5 \times 10^{-8}$ to $10^{-1}$ mole/m$^2$.

A multilayer color photographic light-sensitive material to which the coupler of the present invention can be applied comprises a support having thereon at least one hydrophilic colloid layer as a photographic layer. Examples of hydrophilic colloid layers include photographic subsidiary layers, for example, an intermediate layer, a protective layer, a filter layer, a dye mordanted layer, an antihalation layer, a subbing layer, a layer for preventing contamination of a developer solution, etc. as well as the silver halide emulsion layer, which can contain the coupler of the present invention.

To incorporate an agent for preventing fading of dye images, for example, as disclosed in Belgian Patent No. 777,487, German Patent No. 1,547,684, German Patent Application (OLS) No. 2,146,668, U.S. Pat. Nos. 2,336,327, 2,728,659 and 2,835,579, Japanese Patent Application (OPI) No. 2128/1971, Japanese Patent Application No. 75126/1973, etc. in the intermediate layer, the protective layer or the silver halide emulsion layer described above is particularly effective.

Examples of hydrophilic colloids which can be used in the hydrophilic colloid layer such as the silver halide emulsion layer or the subsidiary hydrophilic colloid layer(s) include, for example, gelatin, colloidal albumin, casein, a cellulose derivative such as carboxymethylcellulose and hydroxyethylcellulose, a polysaccharide derivative such as agar-agar, sodium alginate and a starch derivative, a synthetic hydrophilic colloid such as polyvinyl alcohol, poly-N-vinyl pyrrolidone, polyacrylic acid copolymers and polyacrylamide, or the derivatives or partially hydrolyzed products thereof. If desired, compatible mixtures of these colloids can also be employed. Of these colloids, gelatin is most commonly used. It can be replaced partially or completely by a synthetic polymer, by a so-called gelatin derivative such as those prepared by reacting or modifying the amino, imino, hydroxy or carboxy groups contained, as functional groups, in the gelatin molecule with a compound containing a group capable of reacting with the above-described groups, or a graft gelatin such as those prepared by grafting another polymer chain on the gelatin molecule.

Examples of suitable compounds which can be used for the preparation of the above-described gelatin derivatives include isocyanates, acid chlorides and acid anhydrides such as those described in U.S. Pat. No. 2,614,928; acid anhydrides such as those described in U.S. Pat. No. 3,118,766; bromoacetic acids such as those described in Japanese Patent Publication No. 5514/1964; phenyl glycidyl ethers such as those described in Japanese Patent Publication No. 26845/1967; vinylsulfones such as those described in U.S. Pat. No. 3,132,945; N-allyl-vinylsulfonamides such as those described in British Patent No. 861,414; maleinimides such as those described in U.S. Pat. No. 3,186,846; acrylonitriles such as those described in U.S. Pat. No. 2,594,293; polyalkylene oxides such as those described in U.S. Pat. No. 3,312,553; epoxy compounds such as those described in Japanese Patent Publication No. 26845/1967; esters such as those described in U.S. Pat. No. 2,763,639; and alkane sultones such as those described in British Patent No. 1,033,189.

A wide variety of polymers or copolymers can be employed as polymers to be grafted to gelatin including those obtained from the so-called vinyl monomers such as acrylic acid, methacrylic acid or derivatives thereof, e.g., the esters, amides and nitriles thereof; or styrene. Other examples of suitable polymers are described in U.S. Pat. Nos. 2,763,625, 2,831,767 and 2,956,884; *Polymer Letters*, Vol. 5, page 595 (1967); *Phot. Sci. Eng.*, Vol. 9, page 148 (1965); and *J. Polymer Sci.*, Part A-1, Vol. 9, page 3,199 (1971). Hydrophilic polymers or copolymers having a certain degree of compatibility with gelatin such as those prepared from acrylic acid, acrylamide, methacrylamide, hydroxyalkylacrylates, hydroxyalkylmethacrylates, and the like are particularly preferred.

The photographic light-sensitive material containing the yellow color forming coupler of the present invention can be subjected to color development using an aromatic primary amine compound such as a p-phenylenediamine derivative. Representative examples of color developing agents include N,N-diethyl-p-phenylenediamine, 2-amino-5-diethylaminotoluene, 2-amino-5-(N-ethyl-N-laurylamino)toluene, 4-[N-ethyl-N-(β-hydroxyethyl)amino]aniline, 3-methyl-4-amino-N-ethyl-N-(β-hydroxyethyl)aniline, and the inorganic acid salts thereof, 4-amino-3-methyl-N-ethyl-N-(β-methanesulfonamidoethyl)aniline sesquisulfate monohydrate as described in U.S. Pat. No. 2,193,015, N-(2-amino-5-diethylaminophenylethyl)-methanesulfonamide sulfate as described in U.S. Pat. No. 2,592,364, N,N-dimethyl-p-phenylenediamine hydrochloride, 3-methyl-4-amino-N-ethyl-N-methoxyethylaniline as described in Japanese Patent Application (OPI) No. 64933/1973, and the like. Color developing agents are also described in greater detail in L.F.A. Mason, *Photographic Processing Chemistry*, Pates 226 to 229, Focal Press, London (1966). Also 3-pyrazolidones can be used together with these p-phenylenediamine type developing agents.

The color developer solution can optionally contain various additives. Typical examples of suitable additives include alkaline agents (for example, alkali metal or ammonium hydroxides, carbonates or phosphates); pH-adjusting agents or buffers (for example, weak acids such as acetic acid, boric acid, etc., weak alkalis, or the salts thereof); developing accelerators (for example, various pyridinium compounds or cationic compounds such as those described in U.S. Pat. Nos. 2,648,604 and 3,671,247; potassium nitrate; sodium nitrate; condensation products of polyethylene glycol, and the derivatives thereof such as those described in U.S. Pat. Nos. 2,533,990; 2,577,127 and 2,950,970; nonionic compounds such as polythioethers represented by those described in British Patent Nos. 1,020,033 and 1,020,032; polymeric compounds having sulfite ester groups such as those described in U.S. Pat. No. 3,068,097; organic amines such as pyridine and ethanolamine; benzyl alcohol; hydrazines and the like); anti-figging agents (for example, alkali metal bromides; alkali metal iodides; nitrobenzimidazoles such as those described in U.S. Pat. Nos. 2,496,940 and 2,656,271; mercaptobenzimidazole; 5-methylbenztriazole; 1-phenyl-5-mercaptotetrazole; compounds for use in rapid processing solutions such as those described in U.S. Pat. Nos. 3,113,864; 3,342,596; 3,295,976; 3,615,522 and 3,597,199; thiosulfonyl compounds such as those described in British Patent No. 972,211; phenazine-N-oxides such as those described in Japanese Patent Pub lication No. 41675/1971; those described in *Kagaku Shashin Binran* (*Handbook of Photographic Science*), Vol. II, Pages 29–47 and the like); stain or sludge preventing agents such as those described in U.S. Pat. Nos. 3,161,513 and 3,161,514; and British Patent Nos. 1,030,422; 1,144,481 and 1,251,558; interlayer-effect accelerators disclosed in U.S. Pat. No. 3,536,487; Preservatives (for example, sulfites, bisulfites, hydroxyamine hydrochloride, formsulfite, alkanolamine-sulfite adducts, etc.) and the like.

The couplers of the present invention can be used by addition to such color developer solutions in an amount of about 0.2 to 50 g, preferably 0.5 to 10 g, per liter of the solution.

In case of color reversal light-sensitive materials, a black and white development step is used prior to the color development. Suitable developing agents which can be used include 4-aminophenols such as 4-N-methylaminophenol hemisulfate, 4-N-benzylaminophenol hydrochloride, 4-N,N-diethylaminophenol hydrochloride, 4-aminophenol sulfate, etc.; 3-pyrazolidones such as 1-phenyl-3-pyrazolidone, 4,4-dimethyl-1-phenyl-3-pyrazolidone, 4-methyl-1-phenyl-3-pyrazolidone, etc.; polyhydroxybenzenes such as hydroquinone, 2-methylhydroquinone, 2-phenylhydroquinone, 2-chlorohydroquinone, pyrogallol, catechol, etc.; p-phenylenediamines such as p-phenylenediamine hydrochloride, N,N-diethyl-p-phenylenediamine sulfate, etc.; ascorbic acid; N-(p-hydroxyphenyl)-glycine; and those described in C. E. K. Mees and T. H. James, *The Theory of the Photographic Process*, 3rd Edition, Chapter 13, MacMillan Co., New York (1966) and L. F. A. Mason, *Photographic Processing Chemistry*, Pages 16 to 30, Focal Press (1966). Mixtures of these developing agents can also be used.

After color development, the color photographic materials are subjected to a bleaching. The bleaching can be simultaneously carried out together with the fixing. A bleaching bath can be converted to a blixing bath by adding a fixing agent, if desired. Many compounds can be used as a bleaching agent. Of these bleaching agents, ferricyanides; bichromates; water-soluble iron (III) salts; water-soluble cobalt (III) salts, water-soluble copper (II) salts; water-soluble quinones; nitrosophenol; compounds of a polyvalent metal such as iron (III); cobalt (III); copper (II), etc., especially, complex salts of such a polyvalent cation, and an organic acid, for example, an aminopolycarboxylic acid such as ethylenediaminetetraacetic acid, nitrilotriacetic acid, iminodiacetic acid, N-hydroxyethylethylenediaminetriacetic acid, etc., malonic acid, tartaric acid, malic acid, diglycolic acid and dithioglycolic acid, and 2,6-dipicolinic acid; peracids such as alkylperacids, persulfates, permanganates and peroxides; hypochlorites; chlorine; bromine; and the like can be suitably used, individually or in combination. To the bleaching solution, bleaching accelerators such as those described in U.S. Pat. Nos. 3,042,520 and 3,241,966; and Japanese Patent Publication Nos. 8506/1970 and 8836/1970 and various other additives can be employed.

The processing temperature is determined appropriately according to the kind of photographic materials and the processing steps and sometimes the temperature is lower than about 18° C but usually is higher than about 18° C. Ordinary processing temperatures are about 20° to 60° C and recently about 30° to 60° C. In addition, it is not always necessary to carry out all of the processing steps at the same temperature.

The photographic couplers of the present invention can be applied to a color negative film, a color positive film, a color reversal film, a color printing paper and any other kind of color photographic light-sensitive materials, for example, a color direct positive light-sensitive material, a light-sensitive material for a color diffusion transfer process, a monochromatic light-sensitive material, and the like.

The coupler of the present invention has a high coupling reactivity for an oxidation product of an aromatic arimary amine developing agent and rapidly removes the oxidation product of the developing agent formed during color development, so that the development of the silver halide emulsion is accelerated.

The coupler of the present invention provides, upon coupling with an oxidation product of an aromatic primary amine developing agent, a dye which has superior spectral absorption properties in that it has a pure yellow color without any reddish tint due to less absorption in a longer wavelength region, and thus exhibits an excellent color reproducibility in the subtractive color process. It is considered that these spectral absorption properties are based on the formation of a strong hydrogen bond between the —ZH group in the dye formed from the yellow coupler of the present invention represented by the general formula (I) and the —NH moiety of the amido group in the coupler skeleton (where the —NH moiety of the amido group in the coupler skeleton contributes to the formation of the hydrogen bond, less absorption in a longer wavelength region is obtained as described in G. H. Brown et al, *J. Am. Chem. Soc.*, Vol. 79, page 2923 (1957)).

The dye image formed from the reaction of the coupler of the present invention with an oxidation product of an aromatic amine developing agent is stable and less sensitive to light and humidity, and thus has an extremely less tendency toward fading during storage under severe conditions for a long period of time. Therefore the color photographic image can be stored for a long period of time.

The coupling off group of the coupler of the present invention is not leached out into a developer solution when coupling with a color developing agent in contrast to known two-equivalent couplers. Therefore the coupler does not adversely affect the properties and decrease the storability of the developer due to the acumulation of the coupling off group in the developer.

Further the coupler of the present invention can have a much smaller molecular weight in comparison with known two-equivalent couplers since the coupling off group also acts as a ballasting group. Accordingly, it is possible to reduce the thickness of the photographic light-sensitive material resulting in an improvement in the sharpness of the image, an improvement in the physical properties of the layer due to the decrease in an amount of a coupler solvent used and a shortened period of processing time. Also a decrease in cost of production of the coupler is achieved due to the decrease in the total molecular weight.

The present invention will be further explained in greater detail by reference to the following examples. However, the present invention should not be construed to be only limited to these examples.

EXAMPLE 1

A solution prepared by heating at a temperature of 70° C a mixture of 10 g of Coupler (1) described above, 2-pivaloyl-6-(4-decyloxyphenylsulfonyl)benzomorpholone, 10 ml of di-n-butyl phthalate, 15 ml of cyclohexanone and 0.5 g of sodium di-(2-ethylhexyl)-α-sulfosuccinate was added to 100 ml of an aqueous solution contining 10g of gelatin, and stirred vigorously in a high speed agitator for 20 minutes. The couplers were finely dispersed together with the solvent.

53.7 g of the coupler dispersion was added to 100 g of a photographic emulsion containing $3.0 \times 10^{-2}$ mol of silver iodobromide (iodide content: 2 mol%) and 6 g of gelatin and 10 ml of a 2% aqueous solution of 2-hydroxy-4,6-dichloro-s-triazine sodium salt was added thereto as a hardener. The pH of the mixture was adjusted to 6.5 and then the mixture was coated on a cellulose triacetate support in a silver coated amount of 8.0 mg/100 cm$^2$ . On the layer, a solution prepared by adding 30 ml of the solution of the above described hardener to 1000 ml of an aqueous solution containing 30 g of gelatin was coated, as a protective layer, in a dry thickness of 1.0 micron to prepare a color photographic light-sensitive material. This material was designated Sample A. The sample contained $1.85 \times 10^{-7}$ mol/cm$^2$ of the coupler.

For comparison, a coupler dispersion was prepared using the same procedure as described above except for the use of 10 g of Comparative Coupler (a), α-pivaloyl-2-hydroxy-5-[4-decyloxyphenylsulfonyl]acetanilide, corresponding to Coupler (1), and 53.7 g of the coupler dispersion was mixed with 200 g of a photographic emulsion the same as described above and the mixture was coated in the same manner as described above with a silver coated amount of 16.0 mg/100 cm$^2$ . On the layer, a protective layer as in Sample A is applied to form a color photographic light-sensitive material. This material was designated Sample B. The sample contained $1.87 \times 10^{-7}$ mol/cm$^2$ of the coupler.

These films were subjected to sensitometric stepwise exposure followed by processing in the following manner.

| Processing Step | Temperature (° C) | Time (sec.) |
|---|---|---|
| 1. Color Development | 32 | 240 |
| 2. Water Washing | " | 5 |
| 3. First Fixing | " | 30 |
| 4. Water Washing | " | 120 |
| 5. Bleaching | " | 60 |
| 6. Water Washing | " | 60 |
| 7. Second Fixing | " | 90 |
| 8. Water Washing | " | 90 |
| 9. Drying | — | — |

The compositions of the processing solutions used were as follows.

| Color Developer Solution | |
|---|---|
| Sodium Sulfite | 2 g |
| 4-(N,N-Diethylamino)aniline Sulfate | 1.5 g |
| Sodium Carbonate (monohydrate) | 60 g |
| Potassium Bromide | 1 g |
| Hydroxylamine Hydrochloride | 0.6 g |
| Water to make | 1000 ml |
| First Fixing Solution | |
| Sodium Thiosulfate | 150 g |
| Sodium Sulfite | 15 g |
| Glacial Acetic Acid (28% aqueous solution) | 48 ml |
| Boric Acid | 7.5 g |
| Water to make | 1000 ml |
| Bleaching Solution | |
| Potassium Bromide | 20 g |
| Potassium Ferricyanide | 100 g |
| Glacial Acetic Acid | 20 ml |
| Sodium Acetate | 40 g |
| Water to make | 1000 ml |
| Second Fixing Solution | |
| Sodium Thiosulfate | 200 g |
| Sodium Acetate | 70 g |
| Sodium Sulfite | 15 g |
| Water to make | 1000 ml |

After the processing, the optical density to blue light of these samples was measured thereby the following photographic properties as shown in the following Table wee obtained. The resulting color images, in either case, were clear yellow having an absorption maximum at 439 millimmicrons.

Table 1

| Film Sample | Coupler | Photographic Property | | | Sensitivity* |
|---|---|---|---|---|---|
| | | Fog | Gamma | Maximum Density | |
| A | (1) | 0.17 | 1.98 | 2.45 | 100 |
| B | (a) | 0.18 | 1.54 | 1.92 | 97 |

*Relative value of exposure amount required to provide a density of fog + 0.10.

The maximum densities are shown in Table 2, which were obtained upon processing each sample for different periods of developing time.

Table 2

| | Developing Time vs Maximum Density | | | |
|---|---|---|---|---|
| | | Developing Time (min.) | | |
| Film Sample | Coupler | 2 | 3 | 4 | 5 |
| A | (1) | 1.83 | 2.26 | 2.45 | 2.48 |

Table 2-continued

| | | Developing Time vs Maximum Density | | | |
|---|---|---|---|---|---|
| | | Developing Time (min.) | | | |
| Film Sample | Coupler | 2 | 3 | 4 | 5 |
| B | (a) | 1.02 | 1.61 | 1.92 | 2.09 |

These results obtained show that the coupler used in the present invention provides higher sensitivity, gradation and color density, and provides a sufficient color density in a shortened period of developing time resulting in a decrease in an overall processing time, in comparison with the coupler in which the active methylene group is unsubstituted.

EXAMPLE 2

Each of Samples A and B prepared as described in Exammple 1 was subjected to sensitometric stepwise exposure and then processed in the following manner.

| | Processing Step | Temperature (° C) | Time (min.) |
|---|---|---|---|
| 1. | Color Development | 30 | 6 |
| 2. | Stopping | " | 2 |
| 3. | Water Washing | " | 2 |
| 4. | Blixing | " | 4 |
| 5. | Water Washing | " | 4 |
| 6. | Drying | — | — |

The compositions of the processing solutions used were as follows.

| Color Developer Solution | |
|---|---|
| Benzyl Alcohol | 12 ml |
| Diethylene Glycol | 3.5 ml |
| Sodium Hydroxide | 2 g |
| Sodium Sulfite | 2 g |
| Potassium Bromide | 0.4 g |
| Sodium Chloride | 1 g |
| Borax | 4 g |
| Hydroxylamine Sulfate | 2 g |
| Disodium Ethylenediaminetetraacetate (dihydrate) | 2 g |
| 4-Amino-3-methyl-N-ethyl-N-(β-methane-sulfonamidoethyl)aniline Sesquisulfate (monohydrate) | 5 g |
| Water to make | 1000 ml |
| Stopping Solution | |
| Sodium Thiosulfate | 10 g |
| Ammonium Thiosulfate (70% aqueous solution) | 30 ml |
| Sodium Acetate | 5 g |
| Acetic Acid | 30 ml |
| Potassium Alum | 15 g |
| Water to make | 1000 ml |
| Blixing Solution | |
| Ferric Sulfate | 20 g |
| Disodium Ethylenediaminetetraacetate (dihydrate) | 36 g |
| Sodium Carbonate (monohydrate) | 17 g |
| Sodium Sulfate | 5 g |
| Ammonium Thiosulfate (70% aqueous solution) | 100 ml |
| Boric Acid | 5 g |
| pH was adjusted to 6.8 and water to make | 1000 ml |

After the processing, the optical density to blue light of these samples was measured and then the samples were immersed in the bleaching solution as described in Example 1 for 5 minutes at 30° C followed by washing with water for 10 minutes and drying. The optical density to blue light of these samples thus processed was again measured. The results shown in Table 3 were obtained.

Table 3

| | | Photographic Property | | | | | |
|---|---|---|---|---|---|---|---|
| | | Before Treatment With Potassium Ferricyanide Solution | | | After Treatment With Potassium Ferricyanide Solution | | |
| Film Sample | Coupler | Fog | Gamma | Maximum Density | Fog | Gamma | Maximum Density |
| A | (1) | 0.16 | 1.93 | 2.42 | 0.16 | 1.94 | 2.45 |
| B | (a) | 0.10 | 1.39 | 1.69 | 0.17 | 1.86 | 2.34 |

As can be seen from the results in Table 3, with the coupler used in the present invention, the process of forming dye images is completed during a color development step and a blixing step. On the contrary, with the known coupler in which the active methylene group is unsubstituted, the formation of dye images is only about 70% and 30% of the reaction products still remain in an uncolored form. In order to completely convert the uncolored compounds to the dye, a post-treatment with a strong oxidizing agent is necessary. From the above result it can be understood that the period of color processings is markedly shortened.

EXAMPLE 3

Each of Samples A and B as described in Example 1 was subjected to sensitometric stepwise exposure and then processed in the same manner as described in Example 1 except that the color development was carried out at 32° C for 6 minutes using the color developer solution used in Example 2. The samples thus obtained were stored under conditions at 60° C, 75% relative humidity for 2 weeks and the transmission optical density to blue light of these samples were measured. The results obtained are shown in Table 4.

Table 4

| | | Fastness of Color Image (I) | | |
|---|---|---|---|---|
| Film Sample | Coupler | Remaining Color Image Ratio (%)* | | |
| | | $D_o = 0.5$ | 1.0 | 2.0 |
| A | (1) | 98 | 99 | 100 |
| B | (a) | 97 | 98 | 100 |

*Ratio = $\dfrac{\text{Optical Density after the Storage}}{\text{Optical Density of Fresh Sample}} \times 100$ Also Sample A and B were processed as described above. The samples thus obtained were subjected to storage under exposure to direct sun light for 7 days through a UV-filter which absorbed substantially all light having wave lengths shorter than 400 millimicrons and the light fastness of the color images was measured. The results are shown in Table 5.

Table 5

| | | Fastness of Color Image (II) | | |
|---|---|---|---|---|
| Film Sample | Coupler | Remaining Color Image Ratio (%)* | | |
| | | $D_o = 0.5$ | 1.0 | 2.0 |
| A | (1) | 93 | 95 | 96 |
| B | (a) | 92 | 93 | 95 |

*Ratio = $\dfrac{\text{Optical Density after Exposure}}{\text{Optical Density of Freshly Produced Sample}} \times 100$ These results show that the dye image formed from the coupler of the present invention is superior in stability under conditions of high temperature and high humidity and fastness to light. Further the coupler of the present invention which remains in an unreacted form in a low density area of the image does not adversely affect the stability of dye formed from the coupler to a similar extent to the coupler in which the reactive methylene group is unsubstituted.

EXAMPLE 4

A solution prepared by heating at a temperature of 70° C a mixture of 10 g of Coupler (7) described above, 2-(4-methoxybenzoyl)-6-dodecyloxycarbonylbenzomorpholone, 10 ml of tri-n-hexyl phosphae, 20 ml of butyl acetate and 0.5 g of sodium di-(2-ethylhexyl)-sulfosuccinate was added to 100 ml of an aqueous solution containing 10 g of gelatin and stirred vigorously in a high speed agitator for 20 minutes. The couplers were finely dispersed together with the solvent.

52.2 g of the coupler dispersion was added to 100 g of a photographic emulsion containing $3.0 \times 10^{-2}$ mol of silver iodobromide (iodide content: 5 mol%) and 7 g of gelatin and to which 11 ml of a 2% aqueous solution of 2-hydroxy-4,6-dichloro-s-triazine sodium salt was added as a hardener. The pH of the mixture was adjusted to 6.5 and then the mixture was coated on a cellulose triacetate support in a silver coated amount of 7.0 mg/100 cm², and on the layer, a solution prepared by adding 30 ml of the solution of the above described hardener to 1000 ml of an aqueous solution containing 30 g of gelatin was coated, as a protective layer, in a dry thickness of 1.0 micron to prepare a color photographic light-sensitive material. This material was designated Sample C. The sample contained $1.65 \times 10^{-7}$ mol/cm² of the coupler.

For comparison, a coupler dispersion was prepared using the same procedure as described above except for the use of 10 g of Comparative Coupler (b), α-(4-methoxybenzoyl)-2-hydroxy-5-dodecyloxycarbonylacetanilide, which corresponds to Coupler (7) and 52.2 g of the coupler dispersion was mixed with 200 g and 100 g of the same photographic emulsion as described above and the mixtures were coated in the same manner as described above with a silver coated amount of 14.0 mg/100 cm² and 7.0 mg/100 cm², respectively. On the layer, a protective layer the same as described for Sample C was applied to form two color photographic light-sensitive materials. The former was designated Sample D and the latter was designated Sample E. Sample D contained $1.68 \times 10^{-7}$ mol/cm² of the coupler and Sample E contained $1.67 \times 10^{-7}$ mol/cm² of the coupler.

These films were subjected to sensitometric stepwise exposure followed by processing in the following manner.

| Processing Step | Temperature (° C) | Time (min.) |
|---|---|---|
| 1. Color Development | 24 | 12 |
| 2. Water Washing | " | 4 |
| 3. Fixing | " | 4 |
| 4. Water Washing | " | 4 |
| 5. Bleaching | " | 6 |
| 6. Water Washing | " | 4 |
| 7. Fixing | " | 4 |
| 8. Water Washing | " | 10 |
| 9. Drying | — | — |

The composition of the processing solutions used were as follows.

| Color Developer Solution | |
|---|---|
| Benzyl Alcohol | 5 ml |
| Sodium Hydroxide | 0.5 g |
| Diethylene Glycol | 3 ml |
| Sodium Hexametaphosphate | 2 g |
| Sodium Sulfite | 2 g |
| Potassium Bromide | 2 g |
| 4-Amino-3-methyl-N-ethyl-N-(β-hydroxyethyl) Aniline Monosulfate | 5 g |
| Metaboric Acid | 0.5 g |
| Sodium Metaborate (tetrahydrate) | 77 g |
| Water to make | 1000 ml |
| Fixing Solution | |
| Sodium Hexametaphosphate | 1 g |
| Sodium Sulfite | 5 g |
| Sodium Thiosulfate | 150 g |
| Acetic Acid | 8 ml |
| Water to make | 1000 ml |
| Bleaching Solution | |
| Potassium Ferrocyanide | 8 g |
| Potassium Ferricyanide | 30 g |
| Potassium Bromide | 20 g |
| Borax (pentahydrate) | 15 g |
| Boric Acid | 5 g |
| Disodium Ethylenediaminetetraacetate (dihydrate) | 1 g |
| Water to make | 1000 ml |

After the processing, the transmission optical density to blue light of these samples was measured thereby the results as shown in the following Table were obtained.

Table 6

| Sample | Coupler | Coating Amount of Silver (mg/100cm²) | Coating Amount of Coupler (× 10⁻⁵mol/ 100cm²) | Fog | Gamma | Maximum Density | Sensitivity* |
|---|---|---|---|---|---|---|---|
| C | (7) | 7.0 | 1.65 | 0.15 | 2.07 | 2.68 | 100 |
| D | (b) | 14.0 | 1.68 | 0.14 | 1.85 | 2.45 | 97 |
| E | (b) | 7.0 | 1.67 | 0.12 | 1.51 | 2.03 | 96 |

*Relative value of exposure amount required to provide a density of fog + 0.10.

These results show that the coupler used in the present invention provides a sufficiently high color density even when a small amount of silver halide is used and can be used to reduce the thickness of the emulsion layer in comparison with Coupler (b) in which the active methylene group is unsubstituted. It is advantageous in improving the sharpness of the images and in shortening the period of processing time to use the coupler of the present invention in a yellow dye image forming layer which constitutes an upper layer of a multi-layer photographic light-sensitive material.

EXAMPLE 5

A solution prepared by heating and dissolving at a temperature of 60° C a mixture of 10 g of Coupler (4)

described above, 2-pivaloyl-6-dodecyloxycarbonyl-1-thiabenzomorpholone, 10 ml of acetyl tri-n-butyl citrate and 20 ml of ethyl acetate was added to 100 ml of an aqueous solution containing 10 g of gelatin and 0.5 g of sodium p-dodecylbenzene sulfonate, and stirred vigorously in a high speed agitator for 20 minutes. The couplers were finely dispersed together with the solvent.

65.0 g of the coupler dispersion was added to 100 g of a photographic emulsion for a reversal film containing $4.0 \times 10^{-2}$ mol of silver iodobromide (iodide content: 5 mol%) and 6.5 g of gelatin and to which 11 ml of a 2% aqueous solution of 2-hydroxy-4,6-dechloro-s-triazine sodium salt was added as a hardener. The pH of the mixture was adjusted to 6.0 and then the mixture was coated on a polyethylene terephthalate support in a silver coated amount of 8.0 mg/100cm². To the layer, a gelatin layer was applied, as a protective layer, in a dry thickness of 1 micron to prepare a color photographic light-sensitive material. This material was designated Sample E.

The Sample E was subjected to sensitometric stepwise exposure followed by processing in the following manner.

| Processing Step | Temperature (° C) | Time (min.) |
|---|---|---|
| 1. Pre-Hardening | 38 | 1 |
| 2. Water-Washing | " | 1 |
| 3. First Development | " | 3 |
| 4. Water Washing | " | 0.5 |
| 5. Reversal Exposure | uniform exposure of 8000 lux. sec. to the emulsion surface | |
| 6. Second Development | 38 | 4 |
| 7. Water Washing | " | 1 |
| 8. Bleaching | " | 1 |
| 9. Water Washing | " | 0.5 |
| 10. Fixing | " | 1 |
| 11. Water Washing | " | 1 |
| 12. Drying | — | — |

The compositions of the processing solutions used were as follows:

| Pre-Hardening Solution | |
|---|---|
| Sulfuric Acid (1:1 by volume) | 5.4 ml |
| Sodium Sulfate | 150 g |
| Sodium Acetate | 20 g |
| Pyruvaldehyde (30% aqueous solution) | 15 ml |
| Formalin (37% aqueous solution) | 20 ml |
| Water to make | 1000 ml |
| First Developer Solution | |
| 4-(N-Methylamino)phenol Sulfate | 2 g |
| Sodium Sulfite | 90 g |
| Hydroquinone | 8 g |
| Sodium Carbonate (monohydrate) | 52.5 g |
| Potassium Bromide | 5 g |
| Potassium Thiocyanate | 1 g |
| Water to make | 1000 ml |
| Second Developer Solution | |
| Benzyl Alcohol | 5 ml |
| Sodium Sulfite | 5 g |
| Hydroxylamine Sulfate | 2 g |
| 4-Amino-3-methyl-N-ethyl-N-(β-methane-sulfonamidoethyl)aniline Sesquisulfate (monohydrate) | 1.5 g |
| Potassium Bromide | 1 g |
| Trisodium Phosphate | 3 g |
| Sodium Hydroxide | 0.5 g |
| Ethylenediamine (70% aqueous solution) | 7 ml |
| Water to make | 1000 ml |
| Bleaching Solution | |
| Potassium Ferricyanide | 100 g |
| Sodium Acetate | 40 g |
| Glacial Acetic Acid | 20 ml |
| Potassium Bromide | 30 g |
| Water to make | 1000 ml |
| Fixing Solution | |
| Sodium Thiosulfate | 150 g |

-continued

| Sodium Acetate | 70 g |
|---|---|
| Sodium Sulfite | 10 g |
| Potassium Alum | 20 g |
| Water to make | 1000 ml |

The reversal color image thus obtained has a clear color with an absorption maximum at 442 millimicrons and exhibited excellent color reproducibility.

EXAMPLE 6

A silver iodobromide emulsion (iodide content: 3 mol%) was coated in a dry thickness 5.0 microns and a silver coating amount of 15.0 mg/100 cm² to prepare a film. The film was subjected to sensitometric stepwise exposure and then developed at 32° C for 4 minutes using the developer solution set forth below and followed by fixing, bleaching, fixing, and water washing in the same manner as described in Example 1 to provide a yellow color image.

| Color Developer Solution | |
|---|---|
| Sodium Sulfite | 5 g |
| N,N-Diethyl-p-phenylenediamine Sulfate | 2.5 g |
| Potassium Bromide | 1 g |
| Potassium Iodide (0.1% aqueous solution) | 5 ml |
| Coupler (17), 2-Pivaloyl-6-nitrobenzomorpholone | 2 g |
| Acetone | 20 ml |
| Sodium Hydroxide | 2.5 g |
| Water to make | 1000 ml |

The color image obtained had a clear yellow color with an absorption maximum at 439 millimicrons.

EXAMPLE 7

A solution prepared by heating and dissolving at a temperature of 70° C a mixture of 33.4 g of Coupler (3) described above, 2-pivaloyl-6-dodecyloxycarbonylbenzomorpholone, 35 ml of tris-(2-ethylhexyl)phosphate and 80 ml of butyl acetate was added to 350 ml of an aqueous solution containing 0.2 g of sodium p-dodecylbenzene sulfonate and 35 g of gelatin, and the mixture was stirred. The mixture was then passed five times through a preheated colloid mill. The couplers were finely dispersed together with the solvent.

All of the coupler dispersion was mixed with 1 Kg of a photographic emulsion containing 56.5 g of silver iodobromide (iodide content: 1 mol%) and 60 g of gelatin, to which 45 ml of a 2% acetone solution of triethylene phosphoramide was added as a hardener. The pH of the mixture was adjusted to 6.5 and the mixture was coated in a silver coated amount of 4.0 mg/100 cm² on a baryta coated paper, both surface of which had been resin-coated with polyethylene.

On the coating, a gelatin solution was coated in a dry thickness of 1.0 micron to form a second layer. A green-sensitive silver halide emulsion containing a magenta color forming Coupler (C) was then coated in a dry thickness of 3.5 microns to form a third layer.

Coupler (c)

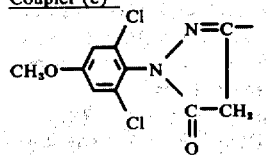

-continued

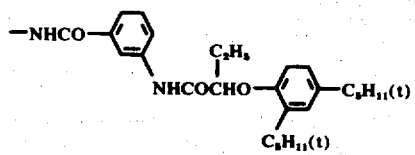

A gelatin solution containing 2-(2'-benzotriazolyl)-4,6-butylphenol as an ultraviolet absorbing agent was then coated in a dry thickness of 2.5 microns to form a fourth layer. A redsensitive silver halide emulsion containing a cyan color forming Coupler (d) of the structure shown below Coupler (d)

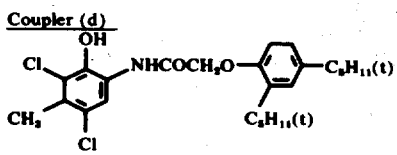

was coated in a dry thickness of 4.0 microns to form a fifth layer and finally a gelatin solution was applied in a dry thickness of 1.0 micron to form the uppermost layer, thereby producing a color printing paper.

This color printing paper was optically printed from a color negative and processed in the same manner as described in Example 2.

The resulting color print had a clear color and had excellent color reproducibility. Particularly, the freedom from any red tint in the yellow color was marked. The yellow dye image had an absorption maximum at 443 millimicrons.

This color print was directly exposed to sun light for 5 days, but, the density decrease for the yellow dye image in the area of an initial reflection density of 1.0 was only 0.04. When it was stored at high temperature hand humidity conditions, i.e. at 60° C, 75% RH, for ten days, no substantial decrease in the density was observed.

gelatin and to which 10 ml of a 2% aqueous solution of 2-hydroxy-4,6-dichloro-s-triazine sodium salt was added as a hardener.

The pH of the mixture was adjusted to 6.5 and then the mixture was coated on a cellulose triacetate support in a silver coated amount of 8.0 mg/100 cm$^2$. On the layer, a solution prepared by adding 30 ml of a solution of the above described hardener to 1000 ml of an aqueous solution containing 30 g of gelatin was coated, as a protective layer, in a dry thickness of 1.0 micron to prepare a color photographic light-sensitive material. This material was designated Sample F. The thickness of the light-sensitive layer of Sample F was 3.9 microns.

For comparison, a film was prepared using the same procedures as described in the production of Sample F except for the use of 10 g of α-4-(4-hydroxyphenylsulfonyl)phenoxy-α-pivaloyl-2-chloro-5-[γ-(2,4-di-tert-amylphenoxy)butyramido]acetanilide instead of the coupler of this invention, which is similar to the coupler of the present invention and is described as Compound Example (31) in U.S. Pat. Nos. 3,408,194 and 3,644,498, in place of Coupler (2) and the use of 86.0 g of the coupler dispersion. This film was designated Sample G. The thickness of the light-sensitive layer of Sample G was 5.0 microns.

Further, another comparative film was prepared using the same procedures as described in the production of Sample F except for the use of 10 g of α-(3-phenyl-2,5-dioxo-1-imidazolidinyl)-α-pivaloyl-2-chloro-5-[γ-(2,4-di-tert-amylphenoxy)butyramido]-acetanilide, which is described as Coupler (6) in Japanese Patent Application (OPI) No. 29432/1973, in place of Coupler (2) and the use of 78.2 g of the coupler dispersion. This film was designated Sample H. The thickness of the light-sensitive layer of Sample H was 4.9 microns.

Samples (F), (G) and (H) were subjected to sensitometric stepwise exposure followed by processing in the same manner as described in Example 4.

After the processing, the transmission optical density to blue light of these samples was measured and the results shown in the following Table were obtained.

Table 7

| Sample | Coupler | AgX/Coupler (molar ratio) | Photographic Property | | | | |
|--------|---------|---------------------------|-----------------------|---|---|---|---|
| | | | Thickness (microns) | Fog | Gamma | Maximum Density | Sensitivity* |
| F | (2) | 4/1 | 3.9 | 0.12 | 1.64 | 2.26 | 100 |
| G | C-(31)** | " | 5.0 | 0.11 | 1.38 | 2.09 | 98 |
| H | C-(6)*** | " | 4.9 | 0.14 | 1.61 | 2.23 | 100 |

*Relative value of exposure amount required to provide a density of fog + 0.10.
**Coupler (31) of U.S. Pat. 3,408,194 for Comparison
***Coupler (6) of Japanese Patent Application (OPI) No. 29432/1973 for comparison.

EXAMPLE 8

A solution prepared by heating and dissolving at a temperature of 70° C a mixture of 10 g of Coupler (2) described above, 2-pivaloyl-6-[γ-(2,4-di-tert-pentylphenoxy)propylcarbamoyl]benzomorpholone, 10 ml of tris-(2-ethylhexyl)phsosphate, 20 ml of cyclohexanone and 0.5 g of sodium di-(2-ethylhexyl)-α-sulfosuccinate was added to 100 ml of an aqueous solution containing 10 g of gelatin, and stirred vigorously in a high speed agitator for 20 minutes. The couplers were finely despersed together with the solvent.

57.9 of the coupler dispersion was added to 100 g of a photographic emulsion containing 3.0 × 10$^{-2}$ mol of silver iodobromide (iodide content: 5 mol%) and 6 g of Further these samples were subjected to sensitometric stepwise exposure followed by processing in the same manner as described in Example 2. The samples thus obtained were subjected to storage under conditions at 60° C, 75% relative humidity for 2 weeks and the transmission optical density to blue light of these samples was measured. The results obtained are shown in Table 8.

Table 8

| Sample | Fastness of Color Image Remaining Color Image Ratio (%)* | | |
|--------|---|---|---|
| | Do = 0.5 | 1.0 | 2.0 |
| F | 99 | 100 | 100 |

Table 8-continued

| Sample | Fastness of Color Image Remaining Color Image Ratio (%)* | | |
|---|---|---|---|
| G | 86 | 91 | 95 |
| H | 98 | 99 | 100 |

*Ratio = $\frac{\text{Optical Density after Storage}}{\text{Optical Density of Fresh Sample}} \times (100)$ The results demonstrate that the coupler according to the present invention can be used to reduce the thickness of the layer in comparison with known couplers in which one hydrogen atom on the active methylene group is substituted with a group capable of releasing upon color development, in order to obtain a cetain color density when the coating amount of silver and the molar ratio of silver halide/coupler are fixed.

The reason for the above is that the amount of coupler, high boiling organic solvent and gelatin used can be reduced due to the relatively small molecular weight of the coupler according to the present invention when the required amount of coupler is coated. Thus the sharpness of the color images formed in the image forming layer(s) which are positioned under a yellow color layer containing the coupler of the present invention in a multilayer color photographic light-sensitive material is advantageously improved.

Further the couplers of the present invention provide color images which are stable under conditions of high temperature and high humidity in comparison with known couplers in which one of the hydrogen atoms on the reactive methylene group is substituted with a coupling releasable group.

While the invention has been described in detail and with reference to specific embodiments thereof, it will be apparent to one skilled in the art that various changes and modifications can be made therein without departing from the spirit and scope thereof.

What is claimed is:

1. A photographic silver halide emulsion containing a yellow color forming photographic coupler as represented by the following general formula (I):

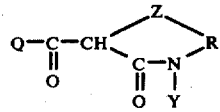

(I)

wherein Q represents a phenyl group, a naphthyl group, a pyridyl group or a furyl group, Y represents a hydrogen atom, an aliphatic group having 1 to 40 carbon atoms, an ali cyclic group, an aromatic group having 6 to 40 carbon atoms or a heterocyclic group having 3 to 40 carbon atoms, R represents a divalent aliphatic group having 1 to 40 carbon atoms, a divalent ali cylic group, a divalent aromatic group having 6 to 40 carbon atoms or a divalent heterocyclic group having 3 to 40 carbon atoms; and Z represents an oxygen atom, a sulfur atom or a nitrogen atom substituted with an acyl group or a sulfonyl group.

2. The photographic emulsion as claimed in claim 1, wherein Q represents an aliphatic group having 1 to 20 carbon atoms.

3. The photographic emulsion as claimed in claim 2, wherein Q represents an unsubstituted alkyl group or an alkyl group substituted with one or more of an alkoxy group, an aryl group, an aryloxy group, an amino group, an acyl group, an acylamino group, an alkylthio group, an arylthio group, a hydroxy group or a halogen atom.

4. The photographic emulsion as claimed in claim 1, wherein said phenyl group is an unsubstituted phenyl group or a phenyl group substituted with one or more of an alkyl group, an alkoxy group, an aryl group, an aryloxy group, an acyl group, an acylamino group, a hydroxy group, a carbamoyl group, a sulfoamido group, a sulfamoyl group, an alkoxycarbonyl group or a halogen atom.

5. The photographic emulsion as claimed in claim 1, wherein Y represents an aliphatic group having 1 to 20 carbon atoms.

6. The photographic emulsion as claimed in claim 5, wherein Y represents an unsubstituted alkyl group or an alkyl group substituted with one or more of an alkoxy group, an aryl group or an aryloxy group.

7. The photographic emulsion as claimed in claim 1, wherein Y represents a phenyl group, a naphthyl group, a pyridyl group or a furyl group, each of which groups may be substituted with one or more of a halogen atom, a nitro group, a cyano group, a thiocyano group, a hydroxy group, an aryloxycarbonylamino group, an alkoxycarbonylamino group, an alkylthio group, an arylthio group, an ureido group, an alkoxy group, an aryloxy group, an alkyl group, an alkenyl group, an aryl group, an amino group, a carboxy group, an acyl group, an alkoxycarbonyl group, an aryloxycarbonyl group, a sulfonyl group, a carbamoyl group, an acylamino group, a sulfo group, an alkylsulfonyl group, an arylsulfonyl group, an alkoxysulfonyl group, an aryloxysulfonyl group, a sulfamoyl group or a sulfonamido group.

8. The photographic emulsion as claimed in claim 1, wherein said coupler is represented by the following general formula (II)

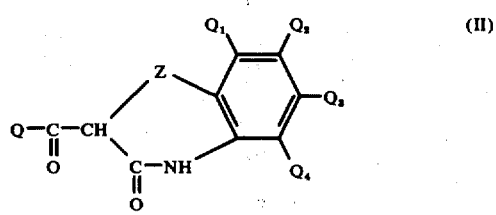

(II)

wherein Q and Z each has the same meaning as defined in claim 1; $Q_1$, $Q_2$, $Q_3$ and $Q_4$, which may be the same or different, each represents a hydrogen atom, a halogen atom, an alkyl group, an alkoxy group, an aryl group, an aryloxy group, an alkoxycarbonyl group, a sulfonyl group, a carbamoyl group, a sulfamoyl group, an alkylamino group, an arylamino group, a sulfoamino group, an acylamino group, a carboxy group, a sulfo group, a cyano group or a hydroxy group.

9. A photographic light-sensitive material which comprises a support having thereon the silver halide emulsion as claimed in claim 1.

10. A photographic light-sensitive material which comprises a support having thereon a red-sensitive silver halide emulsion layer containing a cyan color forming coupler, a green-sensitive silver halide emulsion layer containing a magenta color forming coupler, and a blue-sensitive silver halide emulsion layer containing the photographic emulsion as claimed in claim 1.

11. The photographic emulsion as claimed in claim 1, wherein Y and R when a heterocyclic group are a 5-membered or 6-membered heterocyclic group containing at least one hetero atom selected from the group consisting of a nitrogen atom, an oxygen atom and a sulfur atom which can have a fused ring.

12. The photographic emulsion as claimed in claim 1, wherein Y and R are selected from the group consisting of a phenyl group, a naphthyl group, a pyridyl group or a furyl group, which can be substituted with one or more of a halogen atom, a nitro group, a cyano group, a thiocyano group, a hydroxy group, an aryloxycarbonyl amino group, an alkoxycarbonyl amino group, an alkylthio group, an arylthio group, a ureido group, an alkoxy group, an aryloxy group, an alkyl group, an alkenyl group, an aryl group, an amino group, a carboxy group, an acyl group, an alkoxycarbonyl group, an aryloxycarbonyl group, a sulfonyl group, a carbamoyl group, an acylamino group, a sulfo group, an alkoxysulfonyl group, an aryloxysulfonyl group, a sulfamoyl group, or a sulfoamido group.

13. A method of forming color photographic images which comprises developing an image-exposed photographic silver halide emulsion with a primary aromatic amine color developing agent in the presence of a yellow color forming photographic coupler as represented by the following general formula (I):

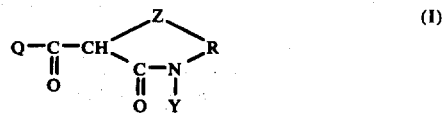

wherein Q represents a phenyl group, a naphthyl group, a pyridyl group or a furyl group, Y represents a hydrogen atom, an aliphatic group having 1 to 40 carbon atoms, an ali cyclic group, an aromatic group having 6 to 40 carbon atoms or a heterocyclic group having 3 to 40 carbon atoms, R represents a divalent aliphatic group having 1 to 40 carbon atoms, a divalent alicylic group, a divalent aromatic group having 6 to 40 carbon atoms or a divalent heterocyclic group having 3 to 40 carbon atoms; and Z represents an oxygen atom, a sulfur atom or a nitrogen atom substituted with an acyl group or a sulfonyl group.

* * * * *